United States Patent [19]

Case et al.

[11] Patent Number: 5,413,915

[45] Date of Patent: May 9, 1995

[54] METHOD AND SENSOR FOR DETECTING TOXIC CHEMICAL EXPOSURE EFFECTS AND METABOLIC ACTIVATION OF CARCINOGENIC CHEMICAL AGENTS

[75] Inventors: George D. Case, Portland, Oreg.; Paul J. Bekowies, Staten Island, N.Y.

[73] Assignee: Resource Technologies Group, Inc., Morgantown, W. Va.

[21] Appl. No.: 729,365

[22] Filed: Jul. 12, 1991

Related U.S. Application Data

[63] Continuation-in-part of Ser. No. 217,862, Jul. 12, 1988, abandoned.

[51] Int. Cl.⁶ .................. C12Q 1/26; C01N 21/00
[52] U.S. Cl. .................................... 435/25; 435/291; 435/317.1; 422/56
[58] Field of Search ............... 435/25, 291, 317.1; 422/68, 86, 56, 57

[56] References Cited

U.S. PATENT DOCUMENTS

| | | | |
|---|---|---|---|
| Re. 30,267 | 5/1980 | Bruschi | 435/12 |
| 3,693,327 | 9/1972 | Scheinberg | 96/151 |
| 3,816,263 | 6/1974 | Rabin et al. | 435/4 |
| 4,071,317 | 1/1978 | Lam | 422/56 |
| 4,078,971 | 3/1978 | Arkles et al. | 435/317.1 |
| 4,205,043 | 5/1980 | Esch et al. | 422/56 |
| 4,258,000 | 3/1981 | Obermayer | 422/55 |
| 4,263,406 | 4/1981 | Bostick et al. | 435/291 |
| 4,275,031 | 6/1981 | Fischer et al. | 422/57 |
| 4,375,515 | 3/1983 | Patel et al. | 435/189 |
| 4,376,820 | 3/1983 | Giannini et al. | 435/4 |
| 4,407,960 | 10/1983 | Tratnyek | 436/1 |
| 4,410,596 | 10/1983 | Whiteside, Jr. et al. | 428/413 |
| 4,421,719 | 12/1983 | Burleigh | 422/57 |
| 4,452,783 | 6/1984 | Marks et al. | 514/19 |
| 4,495,291 | 1/1985 | Lawton | 436/1 |
| 4,526,752 | 7/1985 | Perlman et al. | 422/56 |
| 4,592,896 | 6/1986 | Runnells et al. | 422/109 |
| 4,597,942 | 7/1986 | Meathrel | 422/57 |
| 4,629,697 | 12/1986 | Limbach et al. | 435/26 |
| 4,652,524 | 3/1987 | Modrovich et al. | 435/188 |
| 4,680,165 | 7/1987 | Vo-Dinh | 422/88 |
| 4,792,520 | 12/1988 | Stambrook et al. | 435/6 |
| 5,273,880 | 12/1993 | Schiestl | 435/6 |

OTHER PUBLICATIONS

Case and Crivello, "A Film Badge Biosensor for Hazardous Environmental Chemical Agents," *Proceedings of the 7th National Conference on Hazardous Materials*, May 2–4, 1990, St. Louis, Mo., Hazardous Materials Control Resources Instit., Silver Springs, Md.

Sesardic et al., "The Inducibility and Catalytic Activity of of Cytochromes P450c (P450IA1) and P450d (P450IA2) in Rat Tissues," *Biochem. Pharmacol.* 39:499–506 (1990).

Cohen, "Pulmonary Metabolism of Foreign Compounds: Its Role in Metabolic Activation," *Environ. Health Perspectives* 85:31–41 (1990).

Nebert et al., "The P450 Superfamily: Updated Listing of All Genes and Recommended Nomenclature for the Chromosomal Loci," *DNA* 8:1–13 (1989).

(List continued on next page.)

*Primary Examiner*—Douglas W. Robinson
*Assistant Examiner*—A. Varma
*Attorney, Agent, or Firm*—Klarquist Sparkman Campbell Leigh & Whinston

[57] ABSTRACT

A metabolically active biological component having mixed function oxidation activity. e.g., microsomal P-450 oxidase enzyme complex, is effective in the presence of NADPH and moisture when dispersed in a thin film of a generally neutral hydrophilic film-forming binder. e.g., gelatin, to convert a broad spectrum of carcinogenic substances, into metabolic intermediates, which can be detected, preferably by a colorimetric indicator present in the binder film or an adjacent binder film and undergoing a visible color change. The film or films can be carried, e.g., as spots by a suitable support. e.g., glass or plastic sheet forming a direct-acting self-contained badge-type indicator. The colorimetric indicator is preferably a chemically reduced dye precursor of a polyarylmethane dye or analog thereof, e.g., pararosaniline or malachite green. Such reduced dye precursors are effective colorimetric indicators for organic compounds containing an epoxide structure generally as well as epoxy-containing metabolic intermediates.

17 Claims, 8 Drawing Sheets

OTHER PUBLICATIONS

Nebert et al., "P450 Genes: Structure, Evolution, and Regulation," *Ann. Rev. Biochem.* 56:945–993 (1987).

Ferey et al., "Pararosaniline or Acriflavine-Schiff Staining of Epoxy Embedded Tissue After Periodic Acid Oxidation in Ethanol: A Method Suitable for Morphometric and Fluorometric Analysis of Glycogen," *Stain Technol.* 61:107–110 (1986).

Cresteil et al., "Cytochrome P-450 Isoenzyme Content and Monooxygenase Activities in Rat Liver: Effect of Ontogenesis and Pretreatment by Phenobarbital and 3-Methylcholanthrene," *J. Pharmacol. and Exp. Therap.* 236:269–276 (1986).

Del Monte et al., "Isoprene Metabolism by Liver Microsomal Monooxygenases," *Xenobiotica* 15:591–597 (1985).

Wilson et al., "Binding and Metabolism of Benzo[a]pyrene and 7,12-Dimethylbenz[a]anthracene by Seven Purified Forms of Cytochrome P-450," *Carcinogenesis* 5:1475–1483 (1984).

Girerd et al., "Electronic Properties of the Linear Antiferromagnetically Coupled Clusters [Fe$_3$S$_4$(SR)$_4$]$^{3-}$, Structural Isomers of the [Fe$_3$S$_4$]$^+$ Unit in Iron-Sulfur Proteins," *J. Am. Chem. Soc.* 106:5941–5947 (1984).

Conney, "Induction of Microsomal Enzymes by Foreign Chemicals and Carcinogenesis of Polycyclic Aromatic Hydrocarbons: G. H. A. Clowes Memorial Lecture," *Cancer Res.* 42:4875–4917 (1982).

Rabovsky et al., "Stability of Rat Lung and Liver Microsomal Cytochrome P-450 Enzyme Activities to Storage: Purified Microsomal Fraction, Postmitochondrial Fraction, and Whole Tissue," *J. Toxicol. and Environ. Health* 10:601–611 (1982).

Rinkus et al., "Chemical Characterization of 465 Known or Suspected Carcinogens and Their Correlation with Mutagenic Activity in the *Salmonella typhimurium* System," *Cancer Res.* 39:3289–3318 (1979).

McCann et al., "Detection of Carcinogens as Mutagens in the Salmonella/Microsome Test: Assay of 300 Chemicals," *Proc. Natl. Acad. Sci. USA* 72:5135–5139 (1975).

Sevanian et al., "Microsomal Lipid Peroxidation: The Role of NADPH-Cytochrome P450 Reductase and Cytochrome P450," *Free Rad. Biol. & Med.* 8:145–152 (1990).

Guengerich et al., "Oxidation of Toxic and Carcinogenic Chemicals by Human Cytochrome P-450 Enzymes," *Chem. Res. in Toxicol.* 4:391–407 (1991).

Narhi et al., "Characterization of a Catalytically Self-Sufficient 119,000-Dalton Cytochrome P-450 Monoxygenase Induced by Barbiturates in *Bicillus megaterium*," *J. Biol. Chem.* 261:7160–7169 (1986).

Conney, A. H. "Induction of Microsomal Enzymes by Foreign Chemicals and Carcinogenesis . . ." *Cancer Research* v. 42, pp. 4875–4917, 1982.

METHOD AND SENSOR FOR DETECTING TOXIC CHEMICAL EXPOSURE EFFECTS AND METABOLIC ACTIVATION OF CARCINOGENIC CHEMICAL AGENTS

GOVERNMENT SPONSORSHIP

Work relating to this invention is partially supported by Grant No. 1-R43-ES-OH-03807-01 from National Institute of Environmental Health Sciences, and Contract No. N43-CP-95461 from National Cancer Institute, both of the Public Health Service, U.S. Department of Health and Human Services. The government has certain rights in this invention.

CROSS-REFERENCE TO RELATED APPLICATION

This application is a continuation-in-part of our application Ser. No. 07/217,862, filed Jul. 12, 1988, now abandoned.

FIELD OF THE INVENTION

This invention relates to the detection or monitoring of the presence of carcinogenic substances, either for screening of the potential activity of test substances, as well as the exposure or risk of exposure of persons to such substances in their work environment, and is concerned more particularly with a simple method of achieving such detection which can be embodied into a small portable element, for example, in film or sheet form as a badge or test strip, which can be self-contained and direct acting, thereby providing a prompt indication of exposure, and is sensitive to a broad spectrum of such substances.

BACKGROUND OF THE INVENTION

There is a continuing and even more urgent need for a simple method and means for directly detecting the real or potential activity of chemical substances as carcinogens, including teratogens which are responsible for birth defects. Every year, thousands of new chemicals are developed which require screening for possible carcinogenic or mutagenic activity before approval for their intended purpose. Moreover, more sophisticated scrutiny of presently known and used chemicals initially considered to be benign, gives rise to increasing suspicion as to the hazards presented by their continued utilization calling for fresh evaluation of their acceptability. Further, as the protection of the work force is given increasing national priority, more efficient and more practical ways for determining the existence in the work environment of hazardous chemicals becomes a virtual necessity.

Considerable attention has already been devoted to this need, and a plethora of patents has been issued directed to various of its aspects. In one general category fall badge or strip type monitoring elements, often referred to as dosimeters. The following are a few U.S. patents that are representative of this group:

U.S. Pat. No. 3,693,327—Carbon monoxide is absorbed by a filter comprising hemoglobin which upon saturation undergoes a characteristic change in red coloration;

U.S. Pat. No. 4,205,043—Toxic gases, e.g., in a fire atmosphere, are detected by discs of absorbent material carried on a plastic substrate and covered by a peelable protective film, the discs containing a color-sensitive indicator for reacting with the toxic gas to distinctive color change;

U.S. Pat. No. 4,258,000—A microporous transparent polymeric matrix has its pores filled with a mixture of a solvent for the toxic agent to be detected and a color indicating reactant for reaction with the thus absorbed toxic agent;

U.S. Pat. No. 4,341,642—A partially hydrogenated sequenced styrene-butadiene copolymer undergoes rapid deterioration upon contact with certain organic pollutants, particularly hydrocarbons including halogenated hydrocarbons and oxygenated solvents, the deterioration triggering an indicating signal;

U.S. Pat. No. 4,421,719—A colorimetric indicator sensitive to the presence of a hazardous substance is adhered to a film backing with a high surface area carrier, e.g., alumina or silica, and a self-adhering bentonite clay mineral binder, the selection of the indicator depending on the particular hazardous substance to be detected, such as a permanganate salt for reactive detection of carbon monoxide.

U.S. Pat. No. 4,597,942—Ethylene oxide is detected as a suspect carcinogen by means of a cholesteric liquid crystal composition held in a binder to a substrate, such composition undergoing a characteristic color change when exposed to ethylene oxide; and U.S. Pat. No. 4,680,165—A porous web is impregnated with an agent such as a heavy metal compound, for promoting the absorption and enhancing the phosphorescence of the vapors or aerosols of certain organic chemicals, especially polynuclear aromatic compounds, the absorbed material after a given period being examined for room temperature phosphorescence indicative of the amount absorbed.

Detection elements within this category have the important virtues of light-weight, portability and a generally direct acting response, but their sensitivity is limited to noxious substances for which there is a known companion colorimetric indicator. However, such colorimetric indicators tend to be specific to certain substances to be detected or at least to limited classes of such substances, and the concurrent detection of a broad spectrum of noxious substances in this fashion becomes complicated if not practically impossible.

In an effort to overcome this serious deficiency, researchers in the field have resorted to biological mechanisms to develop what are generally known as "bioassays," one of the most widely used and successful of such assays being commonly referred to as the "Ames test."

The literature is replete with papers relating to the Ames test; a review by Ames appears together with an extensive bibliography as of 1983 in *Cancer*, Volume 53, pages 2034-2040, May 25, 1984. to which reference may be had for more complete information. The Ames test is based on the principle that the mutational tendency of certain strains of bacteria will be altered by exposure to a carcinogenic or mutagenic substance. Specifically, the test employs a mutated strain of *Salmonella typhimurium* which lacks the ability to produce the essential amino acid histidine and consequently is incapable of multiplying when cultured in a nutrient medium lacking this essential nutrient. However, this mutated strain tends to revert to its wild or natural state in which it is able to produce histidine and thus grow when cultured, and this reversionary tendency is significantly increased by contact with a carcinogenic or mutagenic substance. Thus, when the mutated bacterial strain is cultured in contact with the substance to be tested, the reversionary mutagenic effect on the substance can be determined by counting the growth of the test plates and comparing the results against control plates indicative of the spontaneous reversionary tendencies of these bacteria in the absence of the test substance.

The human system, and indeed that of mammals generally, is endowed with many pathways for carrying out the metabolic oxidation of chemical substances into metabolic intermediates which may or may not then be disposed of or possibly subjected to additional pathways of oxidation. These pathways are referred to collectively as "mixed function oxidation" activity and are performed primarily by cells present in the liver and in other organs. According to P. J. O'Brien (Jun. 30, 1988) "Free-Radical-Mediated Chemical Carcinogenesis," *Annals of the New York Academy of Sciences,* volume 534, pp. 552–564, the metabolic intermediates so generated include various combinations of free radicals. They also include epoxides, aldehydes, sulfoxides, hydroxylammonium derivatives, organic aminohydrins and halohydrins, and the like, depending on the parent compound being oxidized. According to D. W. Nebert and F. J. Gonzalez (1987) "P450 Genes, Structure, Function, Evolution and Regulation," *Annual Review of Biochemistry,* Volume 56, pp. 945–993, these oxidations are carried out by at least eight families of membrane-bound enzymes containing cytochromes P-450. Recognizing that it is these ultimate metabolic intermediates that are actually systemically effective rather than the original or starting substance, the Ames test incorporates a metabolically active biological component exhibiting mixed function oxidation activity so as to approximate the multiple natural oxidative pathways occurring within the body so that the response of the bacterial strain is due to the metabolic intermediates generated by this component rather than to the original substance.

The Ames test incorporating the metabolically active biological component having mixed function oxidative activity has been carefully scrutinized and has been found to provide a remarkably good indication of the carcinogenic or mutagenic activity of a broad spectrum of chemical substances and, as of 1983, was said to be in use in thousands of laboratories for this purpose. Its sensitivity is by no means perfect, inasmuch as it is non-responsive to some substances of high recognized toxicity, notably heavy metal compounds, but it certainly represents an important stride forward in the biochemical testing field in expanding the scope of application to a highly useful wide range of different test substances as contrasted with the specificity of dosimeter type test techniques.

Variations and improvements have been made on the Ames test in order to increase its usefulness. In U.S. Pat. No. 4,256,832, instead of visually counting the incubation results of the test plates, the incubation is rather carried out in a controlled oxygen-containing atmosphere from which the consumption of oxygen by the bacteria is detected and taken as a measure of the relative growth of the mutated strains.

In U.S. Pat. No. 4,299,915, the backward acting approach of the Ames test, dependent on the reversionary tendency of a mutated bacterial strain, is replaced by a forward acting assay which determines the effect upon the mutational capability of a different bacterial strain by the presence of the test substance. Here, a strain of *S. typhimurium* naturally possess the ability to enzymatically convert a purine analog, such as 8-azaguanine, into a toxic metabolite which thus inhibits the growth of the bacteria; whereas a mutant of the bacteria lacks the enzymes active on the purine analog, allowing the mutant cells to grow uninhibited when plated, and the mutational change is greater in the presence of a carcinogen or mutagen. Here again, use is made of a metabolically active component similar to that of the Ames test in order to convert the test substance to its ultimate metabolic state.

A somewhat different approach is taken in U.S. Pat. No. 4,072,572 which is based on the capacity of carcinogens or mutagens to decrease the fidelity of in vitro DNA synthesis by DNA polymerases from synthetic polynucleotides incorporating separately labelled correct, complementary nucleotide and incorrect, non-complementary nucleotide. The frequency with which the incorrect nucleotide is incorporated compared to that for the correct nucleotide, represents an "error frequency" indicative of the carcinogenic or mutagenic activity of the test substance present. Again, this procedure envisions the provision of metabolically active biological component having mixed function oxidase activity as in the Ames test for the same reason.

A less related bioassay is covered in U.S. Pat. No. 4,264,729 which presumes that a carcinogenic substance will preferentially promote the growth of cells that are already in a cancerous state compared to healthy tissue. Because the so-called carcinogenic activity of a given test substance tends to be specific for certain types of cancer, the procedure must employ pairs of diseased and healthy tissue from several different sites or organs of the body which are prone to develop cancer, e.g., the lung, breast, ovary, and kidney. This assay is capable of differentiating not only carcinogenic and toxic substances from neutral substances, but also of identifying substances which are specifically anti-cancerous or inhibitive of carcinogenic activity.

It is also known to base bioassays on immunogenic phenomena, one example being U.S. Pat. No. 3,903,898 wherein antibodies against carcinogenic antigenic agents from tobacco smoke are induced in test animals and the resultant antibodies are collected and employed as a filter for absorbing the antigenic agents in tobacco smoke by means of an immunological complexing reaction therewith.

Finally, it is known in U.S. Pat. No. 4,506,752 to utilize a dye in chemically reduced or leuco form, such as the leuco form of methylene blue or triphenylmethane dyes, as a colorimetric indicator for the adventitious entry of oxygen into a sealed oxygen-free package or the like.

Obviously, the Ames test and other bioassays described above must be carried out by skilled personnel and, at best, require a considerable period of time to develop useful results. Consequently, these tests are of limited applicability, notwithstanding the range of substances within their scope.

OBJECTS OF THE INVENTION

The object of the invention is therefore to provide a method and means for evaluating carcinogenic substances which is simple, light-weight, portable, and self-contained so as to be suitable for use on site while being effective for a broad spectrum of such substances.

Another object of the invention is a bioassay adapted to be embodied in badge or strip form and preferably incorporates a colorimetric indicator giving direct visible response to the presence of any of many carcinogenic substances.

A still further object is a simple colorimetric indicating system for epoxide-carrying compounds generally, including epoxidized metabolic intermediates of carcinogenic or mutagenic substances.

SUMMARY OF THE INVENTION

It has now been discovered that quite surprisingly the metabolic activity of the known metabolically active biological component having mixed function activity, as employed in the Ames test and variations thereof, remains active for useful periods of time when incorporated in a layer or film of a hydrophilic film-forming binder, whereby the component is effective to convert carcinogenic substances into their active metabolic intermediate states within such layer or film and that furthermore, the resultant metabolic intermediates when formed can be detected colorimetrically by means of a colorimetric indicator dye precursor derived from well known classes of dyes. Thus, the combination of the metabolically active mixed function oxidation component within the binder film or layer in association with the colorimetric indicating dye precursor retains the beneficial features of both the dosimeter type test devices and the bioassay type procedures, providing broad spectrum sensitivity to a wide variety of test substances in a light-weight highly portable self-contained direct-acting system. The dye precursors are effective colorimetric indicators not only for epoxide-containing metabolic intermediates, a common product of the mixed function oxidation of carcinogenic substances, but of epoxidized compounds generally. The presence of epoxides or epoxidized compounds is a generally good indicator of mutagenic or carcinogenic activity.

DETAILED DESCRIPTION OF THE INVENTION

Figure 1:
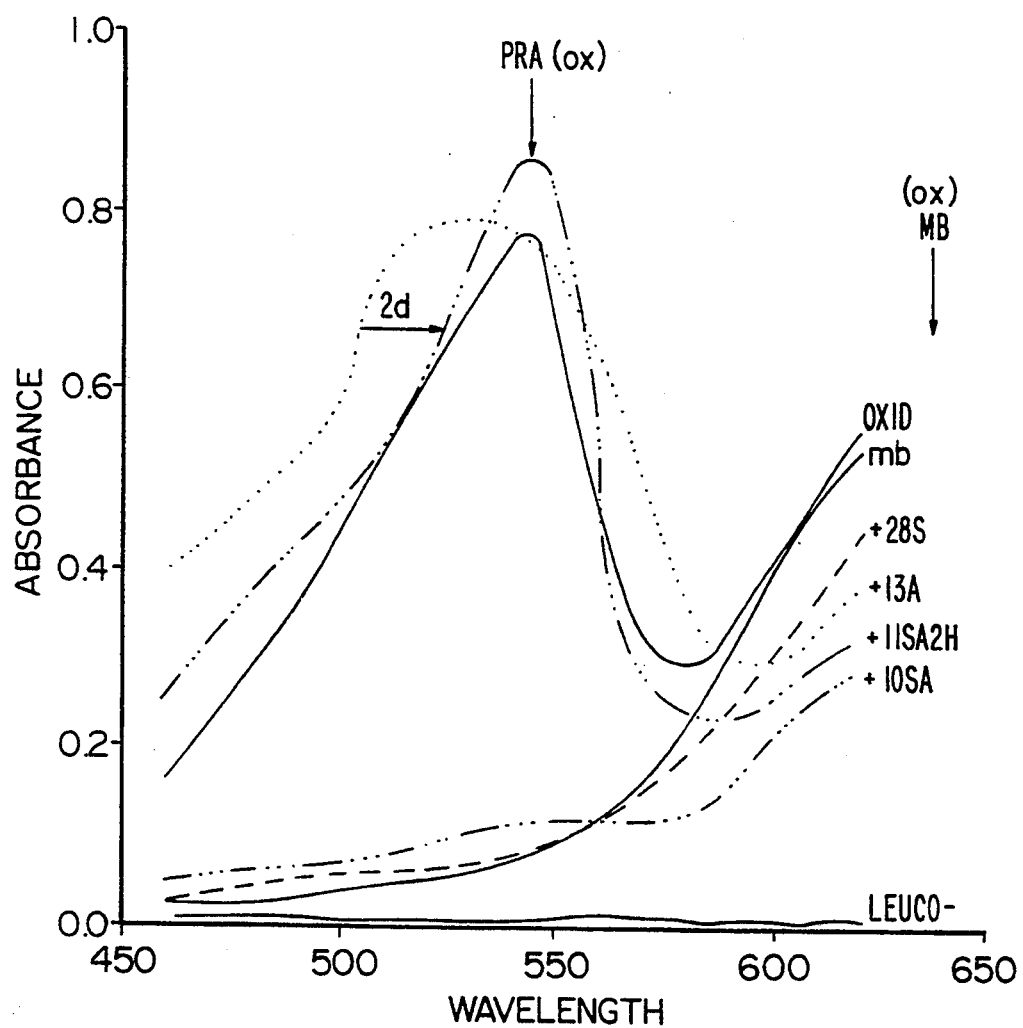
FIG. 1 is a plot of the reduction states of pararosaniline (PRA), a preferred dye for use according to the present invention, versus methylene blue (MB), wherein the plot labeled "leuco" represents the spectra of both dyes in the reduced state; the plot labeled "mb" represents the spectrum of MB in an oxidized state; "oxid" represents the spectrum of a mixed solution of oxidized MB plus fully oxidized PRA; "+28S" represents the spectrum of both dyes at a redox potential of $E_h = +0.028$ V at which MB is partially reduced and PRA is fully bleached; "+10SA" is the "+28S" system after addition of ascorbate which further reduced the MB and oxidized about 10% of the leuco-PRA present; "+11SA2H" represents the "+10SA" system two hours later in which the PRA is fully oxidized; and "+13A" represents partially reduced MB at a clamped redox potential of +0.013 V.

In principle, any biological material or synthetic analog thereof exhibiting significant mixed function oxidation activity will serve as the biological activating component of the invention. According to L. Stryer (1988) *Biochemistry*, 3rd Edition, page 566, mixed function oxidation reactions are catalyzed by enzymes called *monooxygenases* (or mixed-function oxygenases). Monooxygenases participate in the hydroxylation of steroids, phenylalanine, and other compounds. Hydroxylation requires the activation of oxygen. Activation is accomplished by P-450, a specialized cytochrome which absorbs light maximally at 450 nm when it is complexed with CO. Cytochrome P-450 is the terminal component of an electron transport chain in adrenal mitochondria and liver microsomes. NADPH transfers its high-potential electrons ultimately to the oxidized form of cytochrome P-450. The reduced form of P-450 then activates $O_2$. The cytochrome P-450 system is important for the detoxification of foreign substances (xenobiotic compounds). For example, the hydroxylation of phenobarbital, a barbiturate, increases its solubility and facilitates its excretion. Likewise, polycyclic aromatic hydrocarbons are hydroxylated by the P-450 system. However, the action of the P-450 system is not always beneficial. Some of the most powerful carcinogens are converted in vivo into a chemically reactive form. This process of metabolic activation is usually carried out by the P-450 system.

According to D. W. Nebert, D. R. Nelson, M. Adesnik, M. J. Coon, R. W. Estabrook, F. J. Gonzalez, F. P. Guengerich, I. C. Gunsalus, E. F. Johnson, B. Kemper, W. Levin, I. R. Phillips, R. Sato, and M. R. Waterman (January 1989) "The P450 Superfamily: Updated Listing of All Genes and Recommended Nomenclature for the Chromosomal Loci," *DNA,* Volume 8: 1–13, cytochrome P-450 enzymes in mammals are encoded by several families of genes, and at least seventy-one variants are known. Cytochrome P-450 nomenclature has recently been standardized according to genetic lineage. For the purpose of detecting environmental chemical hazards, a material with cytochrome P450IA or P450IIC properties (Nebert and Gonzalez, 1987, *op cit*) is most desired, although other variants may be useful for special purposes. Preferably, this component is the same as in the prior art Ames test and its variations and is constituted by microsomes which are subcellular organelles constituted of endoplasmic reticulum isolated by selective centrifugation of massively disrupted cells obtained from various organs of the body. The liver is an especially efficient source of microsomes, having a content of about 60% by weight microsomes, while lung contains about 20%. Microsomes are also found in other organs such as the brain or adrenal gland which has a level of about 10%, as well as muscle tissue which contains a very small amount, but for obvious practical reasons, the liver and lung are the preferred sources. These organs are normally obtained from laboratory animals, the same organs from deceased humans would be suitable if available. The composition and metabolic activity spectrum of mixed-function oxidases in these preparations can be altered by the introduction of appropriate inducing agents, for example, by intraperitoneal injection a short time prior to recovery of the microsomes. As an example, administration of environmental pollutants such as polycyclic aromatic hydrocarbons or polyhalogenated benzo-p-dioxins results in microsomes enriched in cytochrome P-450 isozymes with aryl hydrocarbon hydroxylase ("AHH") activity (Nebert and Gonzalez, 1987, *op cit*) and according to A. H. Conney (1982) "Induction of Microsomal Enzymes by Foreign Chemicals and Carcinogenesis by Polycyclic Aromatic Hydrocarbons," *Cancer Research,* Volume 42: pp. 4875–4917, thus simulate the metabolic activation profile of heavy smokers.

In general, microsomes are recovered in the following manner. The experimental animal source, e.g., rat, is killed, ordinarily by decapitation, and its liver excised optionally together with the lung. These organs are entirely masticized in a suitable buffer salt solution, and this suspension is subjected to multi-stage centrifugation. The first stage is carried out at 1,000 g where g represents one unit of gravitational force. The sediment from this stage contains the cell debris and nucleic material from the organ and is discarded. The supernatant contains the microsomes and is subjected to a second stage of centrifugation, which is in the range of about 10,000–16,000 g. The sediment from this stage contains the mitochondria and is discarded, while the microsome containing supernatant is subjected to a final ultra-centrifugation stage at 105,000 g. The ultracentrifugation sediment material is constituted of the microsomes, while the supernatant liquid from that stage is discarded. The microsome material thus recovered is then re-suspended in the buffer solution.

A specific procedure found suitable for isolating microsomes is as follows:

Microsome preparations were obtained from rat liver according to the procedure of Wright and others. Male Sprague-Dawley rats (Miller-Zivic Laboratories, Pittsburgh, Pa.), average weight of 250–350 gm, were decapitated, and livers excised immediately and perfused with ice-cold 0.9% phosphate buffer (0.081M $K_2HPO_4$ and 0.019M $KH_2PO_4$, pH=7.4), using a Potter-Elvejehem homogenizer. After removal of nuclear and mitochondrial fractions by differential centrifugation, liver microsomes were pelleted by centrifugation at 105,000 g for 75 min. The pellets, containing the microsomes, were then suspended in 0.10M phosphate buffer, pH=7.4, or alternate media as indicated.

A preferred modification of this procedure is as follows:

Livers are excised from decapitated Sprague-Dawley female rats, phosphate buffer, pH=7.4 with 1.15% KCl and 1 mM EDTA, with a teflon pestle and glass homogenizer for 30 sec at 4° C. After homogenization, the suspension is centrifuged at 10,000 g for 10 min, and the supernatant from this stage is re-centrifuged at 105,000 g for 90 min. Sediment from this stage, in pellet-like form, is resuspended in water.

It is desirable that all water employed in these procedures be glass distilled and then deionized by passage through a mixed-bed ion exchange resin, activated charcoal and finally through a 0.22 micrometer filter to a conductivity level corresponding to an 18 MOhm resistance.

Experimental procedures for recovering microsomes are commonly found in the literature of which two representative examples treating mixtures of liver and lung tissue are the following: "Cytosolic Factors Which Affect Microsome Lipid Peroxidation in Lung and Liver," by Wright, Colby and Miles, in *Archives of Biochemistry and Biophysics,* Volume 206, No. 2, pp. 296–304, February 1981; and "Stability of Rat Lung and Liver Microsomal P-450 Enzyme Activities to Storage: Purified Microsomal Fraction, Postmitochondrial Fraction, and Whole Tissue," by Danner-Robovsky and Groseclose, *Journal of Toxicology and Environmental Health,* Volume 10, pages 601–611, 1982. As the latter paper states, the isolated microsomal fraction can, as an alternative to immediate use while fresh, be stored by rapid freezing in liquid nitrogen followed by storage in -70 to 80° C. Thawing of the thus frozen samples is carried out by placing them at 4° C. so that thawing proceeds gradually, e.g., overnight.

Another effective material possessing mixed-function oxidation activity is purified cytochrome P-450, which is a mixed function oxidase enzyme complex contained by microsomes and responsible to a major extent for the mixed function oxidation activity of these organelles. Cytochrome P-450 can be isolated and purified from the microsomes by techniques already proposed in the literature (N. M. Wilson, M. Cristou, C. R. Turner, S. A. Wrighton, and C. A. Jeffcoate (1984) "Binding and Metabolism of Benzo(a)pyrene and 7,12-Dimethylbenzanthracene by Seven Purified Forms of Cytochrome P-450," *Carcinogenesis,* Volume 5: pp 1475–1483.) and employed directly as the effective biological activating component of the invention. Synthetic analogs of numerous electron-transferring enzymes, of which cytochrome P450 and its reductase are but two examples, have been reported in the literature. Examples include synthetic iron-sulfur clusters such as trinuclear ferredoxin analogues reported by J. J. Girerd, G. C. Papaefthymiou, A. D. Watson, E. Gamp, N. Edelstein, R. B. Frankel, and R. H. Holm (1984) "Electronic Properties of the Linear Antiferromagnetically Coupled Clusters $[Fe_3S_4(SR)_4]^{3-}$, Structural Isomers of the $[Fe_3S_4]^+$ Unit in Iron Sulfur Proteins," *Journal of the American Chemical Society*, Volume 106: pages 5941–5947, of which certain relatives include low-potential electron transfer enzymes such as NADPH-cytochrome P450 reductase.

While the microsomes are preferably used in purified form free of the supernatant (cytosol) after the ultracentrifugation stage, the supernatant from the preceding stage after separation of the mitochondrial material, sometimes referred to as the post-mitochondrial fraction or "S-9," can also be employed directly.

Any other biochemically active material exhibiting mixed function oxidation activity can in principle be substituted for the microsomes of the cytochrome P-450 extracted therefrom as the same may become available either presently or in the future. Such equivalent materials can be identified by ways known in the art.

As a biological material, the microsomes or their equivalent are subject to a somewhat limited storage life, but at worst their storage life is sufficiently long as to be useful in practice, their normal life under ambient conditions being about 24 hours. However, it is readily possible through proper purification techniques, such as deionization chromatography, or by resort to storage at refrigeration or freezing temperatures to significantly increase their storage stability. This is demonstrated by the following comparative evaluation of the effects of both a deionization treatment and storage temperature on the stability of microsomes, using a known test for identifying benzo(a)pyrene metabolites via fluorescence.

Microsomes from rat liver were suspended into each of a buffer solution (pH=7.4) or into a 0.3M sucrose solution containing 5 mM equimolar tris(hydroxymethyl-)aminomethane ("TRIS") and morpholinopropanesulfonic acid ("MOPS"). Microsomes in the latter solution were then deionized by elution through a succession of columns containing a mixed-bed ion exchange resin marketed under the trade name DOWEX MR-3C, until the pH of the eluate remained constant. Both suspensions were then split into two aliquots, one of which was stored at room temperature and the other of which was kept refrigerated at 4° C. The ability of each of these microsome preparations to effect the metabolic oxidation of benzo(a)pyrene to fluorescent hydroxylated products, was then measured as a function of storage time. The hydroxylated metabolic product of benzo(a)pyrene exhibits a distinctive yellow fluorescence in contrast with the pale blue fluorescence normally emitted by the parent compound so that a measure of the intensity of this yellow fluorescence, expressed in counts per minute, indicates the metabolically active fraction of the microsomes remaining after the specified storage interval, the results of such comparison being tabulated in the following Table 1.

It is important that the pH of the media containing the microsomes, both during their preparation as well as suspension in the film or layer of the invention, be maintained generally neutral, although some tolerance for slight alkalinity does exist. An acceptable pH range is thus about pH 6.5 to about pH 9.0, although the deionization treatment referred to above increases the tolerance of the microsomes for slight acid pH's down to about 6.0.

TABLE 1

Effect of Deionization Treatment and Storage Temperature on Microsomal Stability

| Storage Conditions: Time at Temperature | Hydroxylated Benzo(a)pyrene Production, as Fluorescence Counts per Minute per 0.03 mM Microsomal Cytochrome P450 Present | |
|---|---|---|
| | UNTREATED | DEIONIZED |
| 3 Hours at 22° C. | 500 | 556 |
| 16 Hours at 22° C. | 310 | 485 |
| 120 Hours at 4° C. | 36 | 478 |

In order to maintain this generally neutral pH in the media containing the microsomes, appropriate buffer salts already well known in the art can be employed.

The concentration of the microsomes for purposes of the invention can vary considerably from perhaps as low as 1 mg/mL of the liquid film-forming medium up to as high as 100 mg/mL or perhaps even higher. Typically, a concentration of about 5–10 mg/mL has been found particularly useful in practice, and as a general rule, any concentration known to be suitable for the execution of the Ames test will be equally acceptable for the practice of this invention.

An essential condition to the mixed function oxidation activity of the biologically active component of the invention, e.g., microsomes, is the presence of the cofactor nicotinamide adenine dinucleotide phosphate and that the cofactor be in its reduced form (NADPH) rather than its oxidized form (NADP). This same condition appears to apply to the Ames test as well. The amount of NADPH can vary, with a range of about 1–20 mg/mL of the film-forming medium being suitable. Alternatively, 5 millimols/L is effective. The NADPH appears to participate in the metabolic oxidation activity as an essential reactant whose absence renders the mechanism inoperative. Presently, no practical substitute for NADPH has been identified but may become available in the future. The microsomes and NADPH function cooperatively in the system of the invention and consequently should be considered in the same film or layer if plural films or layers are employed.

Any hydrophilic film-forming organic binder can be employed as the film-forming medium in which the microsomes or equivalent are dispersed or embedded in the presence of NADPH. A preferred hydrophilic binder is gelatin, but hydrophllic synthetic polymers known to be generally equivalent to gelatin in the photographic field can be substituted, including such hydrophllic polymers as polyvinyl alcohol, polyvinylpyrrolidone, and acrylic acid polymers in neutral salt form. The thickness of the film layer of the hydrophilic binder material is not critical, provided that the thickness is sufficient to make available an effective concentration of the biologically active component. Very thin layers down to 0.0076 mm or less are useful, but much thicker layers up to or even exceeding 1 mm are also permissible. Thinner layers tend to be preferred because diffusion of the test chemical therethrough proceeds more rapidly and a lesser thickness of about 10 micrometers is fully satisfactory. The binder must meet the requirement of generally neutral pH stated above and should otherwise be inert with respect to the active component present. The gelatin or other binder is dissolved in water to produce the film-forming medium, the concentration being mainly dependent on the desired thickness of the film that remains after drying.

The result of the mixed function oxidation activity of the biologically active component, e.g., microsomes, is the formation of various metabolic intermediates or derivatives of the carcinogenic substances, of which the epoxide and aldehyde derivatives are of paramount importance (Nebert and Gonzalez, 1987, op cit). An epoxidized intermediate can be created by mono-oxygen addition across a carbon double bond such as is contained in a great number of organic compounds particularly those of actual or suspected carcinogenic activity. Thus, exposure of the biologically active component to the carcinogenic substance can be determined by detecting the presence of characteristic metabolic intermediates in the film layer after exposure of the same to the test environment. Likewise, an oxidized intermediate with free-radical characteristics can be created, by reaction of the cytochrome P-450-bound oxygen or with a ferryl form of cytochrome P-450.

A preferred technique for identifying the presence of the metabolic intermediate derivative from the carcinogenic substance involves the provision of a colorimetric indicator as a component of the inventive system. Effective colorimetric indication can be achieved by means of a dye capable of undergoing reversible chemical oxidation-chemical reduction or conjugation reactions and which exhibits visibly distinct colorations in these respective states. Thus, the dyestuff is converted by chemical reduction to its reduced state wherein it serves as a dye precursor capable of undergoing subsequent oxidation or conjugation with a concomitant color change. A preferred dye of this type is pararosaniline (PRA) which upon treatment with a suitable chemical reducing agent, such as sodium sulfite, is converted, i.e. bleached, to a colorless or leuco state from its normal generally magenta coloration in its oxidized dye salt state. Pararosaniline is commonly employed as a stain in biochemical procedures and being thus readily available, performs quite effectively for purposes of the invention. This dye is the simplest member of a class of dyes known as triphenylmethane dyes which together with their diphenyl analogs are known to behave chemically as a group. Thus, any of other such members of this class of dyes would be effective as a colorimetric indicating dye in the invention. Examples of other such members of this class include Fuschine, Malachite Green, Crystal Violet, Methyl Violet, Methyl Green, and Auramine. All of the dyes in this group upon chemical reduction are converted to their leuco state and are thus colorless, and the change upon subsequent oxidation or conjugation to a colored state is hence readily visible. However, it is not essential that the dye precursor in its reduced state be necessarily free of coloration so long as its color in that state contrasts significantly with its color in its final oxidized dye salt state. It should perhaps be noted that to avoid confusion, the behavior of the preferred polyarylmethane dyes in the context of this invention differs somewhat from the behavior which they normally exhibit in actual dye chemistry as in the dyeing of textiles. In the usual dyeing mechanism, the polyarylmethane dyestuffs starting from their normal color dye salt condition, e.g. chloride, are converted to their colorless carbinol state by reaction with alkali from which they can be reduced by chemical reduction to their leuco state. From the latter state, the reaction sequence is reversible, first by a chemical oxidation to reach the colorless carbinol condition and then by a salt forming reaction, e.g., with an acid such as hydrochloric acid, to produce the colored dye salt state. The inventive precursor forming mechanism, in contrast, proceeds directly from the colored dye salt state to the chemically reduced colorless leuco state without passing through the neutralized carbinol state. As an example, the leuco state can be formed in the presence of a 1–100 fold molar excess of sodium sulfite or the like and NADPH, and maintained therein in the presence of air.

It is believed that other dyes capable of reversible reduction-oxidation with different colorations in these respective states are available and can be used in the practice of this invention. However, certain classes of dyes must be disqualified as candidates for this purpose because they are themselves chemical targets of the mixed function oxidation reactions associated with carcinogenicity or related toxic effects. Thus, dyes in such classes as the acridines, substituted anilines or quinolines must be excluded, and in general any dyestuff which has polyaromatic amine structure, i.e., includes a condensed ring system, would be of dubious value in this invention. Thus, any dye precursor which is directly attacked by the metabolically active component, i.e., microsomes, would yield a false positive indication and should be excluded. Similarly, some reduced, i.e., leuco dye precursors are prone to rapid oxidation in air and would develop color prematurely. Slow redox mediation kinetics, reflected by partial reversibility of oxidation-reduction as in the case of triphenylmethane dyes reported by W. Kemula and A. Axt (1969) "Electrochemical and Spectroscopic Investigations of Triphenylmethane Dyes: I. Electrochemical Investigations," *Rocz. Chem.*, Volume 43:, no. 1: pp. 199–207. *Chem. Abstr.* 71, 4495d, are a desirable feature. Hence, the dye precursor should be relatively stable against spontaneous oxidation in air.

Diphenylmethane and triphenylmethane dyes of the present invention have midpoint oxidation-reduction ("redox") potentials ("$E_{m7}$") apparently more negative than the $E_{m7}$ value for NADPH or cytochrome P450 isozymes. Therefore, these dyes do not interfere with electron flow during the initial metabolic activation steps. Specific examples include pararosaniline ($E_{\frac{1}{2}} = -0.75$ V) and malachite green ($E_{\frac{1}{2}} = -0.55$ V) (W. Kemula and A. Axt (1969) op cit; Also H. O. Willard, L. L. Merritt, and J. A. Dean (1965) *Instrumental Methods of Analysis*, 4th Ed., pp. 682–685 and 760–763, for a comparison of $E_{\frac{1}{2}}$ versus $E_{m7}$. These potentials are too negative for direct measurement in water, as $E_{m7} = -0.42$ V for water breakdown to hydrogen.), both of which respond with color development upon microsomal metabolic activation.

A further requirement of the dye chosen as a color coupling indicator is a capability to prevent spontaneous air oxidation in the absence of a microsomal activation trigger—slow mediation as reported by M. Spiro (1964) "Standard Exchange Current Densities of Redox Systems at Platinum Electrodes," *Electrochimica Acta* 9: 1531–1537. *Chem. Abstr.* 62: 232 g. Slow mediation is demonstrated in the following example (FIG. 1).

Solutions containing approximately 0.02 mM pararosaniline and 0.03 mM methylene blue ($E_{m7} = +0.01$ V) in a 50 mM sodium phosphate buffer standard, were scanned spectrophotometrically, and subsequently reduced with either 0.2–0.5 mg solid sodium dithionite ($E_{m7} << -0.5$ V) or 0.5–1.0 mM sodium ascorbate ($E_{m7} = +0.08$ V. see Stryer, 1988, op cit). Methylene blue is a rapidly mediating redox indicator, and as such is conventionally used for standardization of electrodes and electrochemical systems used in redox potentiometry. Systems containing ascorbate were therefore tightly clamped at a redox potential of +10 to +20 mV, regardless of any interfering influences such as oxygen. FIG. 1 shows the results. The reduced dyes (both methylene blue and pararosaniline, irrespectively) exhibit no visible absorption ("leuco" curve in FIG. 1) at any wavelength between 450 nm and 650 nm. Spectrum "mb" is that of pure methylene blue in its oxidized state. Curve "oxid" is the spectrum of a mixed solution of methylene blue as in curve "mb" plus the fully oxidized pararosaniline. Addition of sodium dithionite to the maintained in the leuco-state. A comparison of the performance characteristics of detection elements prepared using various leuco dyes and dye precursors is given in the following example of Table 2. Two of the test dyes, methyl green ($E_{\frac{1}{2}}$ approximately $-0.55$ V, similar to malachite green) and methyl violet ($E_{\frac{1}{2}}$ approximately $-0.75$ V, similar to pararosaniline), are members of the class of triarylmethane dyes. Two other test dyes, Nile Blue A ($E_{m7} = -0.12$ V) and Safranin O ($E_{m7} = -0.28$ V), are well known redox mediators. Nitro Blue Tetrazolium (NBTZ) is a well known trapping agent for the free radical anion superoxide

TABLE 2

Color Development in Detection Elements with Different Leuco Dyes

| Test Chemical, with Applied Dose, μmol | Methyl Green | Methyl Violet | Naphthol Blue-Black | Nile Blue A | NBTZ | Safranin O |
|---|---|---|---|---|---|---|
| | Color of Test Spot for Respective Leuco Dye | | | | | |
| None; oxidized dye color | Green | Violet | Black | Blue | Clear | Red |
| None; leuco dye spot only, no overlay | Clear | Clear/pale violet | Clear | Pale Blue | Pale yellow | Pink |
| None; unexposed controls (microsome overlay) | Clear | Clear/pale violet | Clear | Pale Blue | Black | Pink |
| | New Color Development | | | | | |
| CH$_3$CCl$_3$, 10 | None | None$^{a,b}$ | None | None | Black | None |
| Menadione, 10 | None | None$^{a,b}$ | None$^b$ | None$^b$ | Black | None |
| Formaldehyde, 1 | Bright green | Violet | None | Blue | Black | None |
| Hydrazine, 10 | $c$ | $c$ | $c$ | $c$ | Black | $c$ |
| Ergosterol, 10 | Green | Violet | None | Blue | Black | Pink |
| ICH$_2$COOH, 10 | Green | Purple | None | Med. blue | Black | None |
| Concordance to PRA | 3/5 | 4/5 | 1/5 | 4/5 | 0/5 | 1/5 |

$^a$Color development observed within first 18 hours after exposure of test spot to chemical substance.
$^b$Latent color development (weak positive), apparent within six months after exposure of test spot to chemical substance.
$^c$Negative direction for color development, i.e., further disappearance of color inherently present in unexposed test spots.

"oxid" sample resulted initially in the partial reduction of methylene blue, but total bleaching of pararosaniline (curve "+28S," indicating a system redox potential of $E_h = +0.028$ V). Subsequent addition (See above) of ascorbate to this system elicited further reduction of the methylene blue, but also, over a 5–10 minute period, gave rise to an oxidation of approximately 10% of the leuco-pararosaniline present (Curve +10SA). Two hours later, without any further chemical additions, the same sample showed 100% oxidized pararosaniline, but a clamped redox potential at $E_h = +0.0115 +/- 0.0015$ V (Curve +11SA2H). Ascorbate, by itself, does not reduce pararosaniline, although it does reduce methylene blue partially (Curve +13A, indicating a clamped redox potential of +0.013 V. The shifted absorption spectrum of +13A reverts within 1–2 days to a spectrum similar to curve +11SA2H.). The FIG. 1 data indicate a standard oxidation-reduction potential ($E_{m7}$) substantially more negative than $-0.1$ V for pararosaniline in aqueous media. These results suggest a rapid quasi-reversible mechanism for triarylmethane dye reduction by sulfurous compounds, which is not kinetically linked to the state of the redox mediator methylene blue, nor of oxygen. The fact that pararosaniline required some two hours to equilibrate with respect in a redox voltage-clamped system demonstrates its slow mediation rate.

Few low-potential dyes can be so maintained. Viologen dyes mediate so rapidly that they serve as excellent redox indicators, but cannot be maintained in an aerobic system. However, triarylmethane dyes are more easily ($O_2^-$), giving a formazan reaction product. Naphthol Blue Black is a polyaromatic aminophenol derivative conventionally employed as a common stain, with slow mediating redox properties, but which by virtue of its structure may be vulnerable to chemical attack in the microsomal monooxygenase reactions.

Solutions containing 0.5 mM of the respective dyes in 0.1 M TRIS buffer, pH=7.4 (except for nitro blue tetrazolium, 5.0 mM in 50% ethanolic TRIS, pH=7.4) were bleached with a few crystals of sodium sulfite or sodium dithionite, then plied in 0.02 mL aliquots as test spots on a clear sheet of transparency film. Spontaneous color development in air was noted (Table 2). Subsequently, a suspension of rat liver microsomes containing 1 mM NADPH and 1 mg/mL gelatin in 0.1 M TRIS-MOPS buffer (pH=7.7) was plied in 0.05 mL aliquots over the dried leuco-dye test spots. After drying, color development condition was noted, and the test spots saved for exposure tests to chemical substances (Table 2). Exposures were carried out by layering 0.01 mL of 0.1–1.0 M solutions of test chemical substances onto the test spots, and changes in color noted over time.

The nitro blue tetrazolium test spots developed a purple/black coloration immediately upon addition of the microsome/NADPH layer (Table 2), indicative of a superoxide generating reaction in the metabolically active biological component. Superoxide production by cytochrome P-450 containing systems has been alluded to in the literature. Since no further indicating reaction occurred following exposure to the test chemical agents (Table 2), determination of superoxide as a metabolic activation intermediate is not useful for the detection of hazardous or carcinogenic chemical substances.

Color development responses of the other test spots to the Table 2 chemical substances vary among the respective leuco-dyes. For comparison, from separate experiments, test spots containing leuco-PRA give positive color responses to all of the Table 2 chemical substances with the exception of $CH_3CCl_3$. Methyl violet, a pentamethyl- derivative of PRA, gives the closest concordance to PRA response, but might give a more sensitive response to $CH_3CCl_3$. It is followed in activity by Nile blue A and methyl green. In separate tests with detection elements using leuco forms of malachite green, exposure to hydrazine solutions elicits a visually detectable green color. Detection elements containing the leucoforms of methylene blue in combination with pararosaniline, when exposed to hydrazine in like manner, develop a magenta color characteristic of the pararosaniline product, and not a blue coloration characteristic of methylene blue oxidation. As a group, triarylmethanes and diarylmethanes appear to give the most reliable response to hazardous or carcinogenic chemical substances among leuco dyes. Variances among individual members of the this group of indicating dyes is to be expected; their detection response to hydrazine being a particularly relevant test criterion. Among dyes in the general class of phenazines (e.g., safranines), phenothiazines (e.g., methylene blue), and phenoxazines; Nile blue A (a phenoxazine derivative) exhibits a reasonably good correspondence with hazardous chemical substance indication.

The chemical reactions which are believed to take place in the practice of the preferred embodiment of the invention ensue from well known mixed-function oxidation processes (Nebert and Gonzalez, 1987, op cit, Table 1 on page 950) triggered directly or indirectly by environmental agents, and include those represented by the following schematic equations, where [CHEM] represents the molecules of the hazardous or carcinogenic chemical substance to be tested, $O_2$ is atmospheric oxygen and m denotes the action of microsomes:

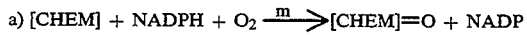
a) [CHEM] + NADPH + $O_2$ $\xrightarrow{m}$ [CHEM]=O + NADP

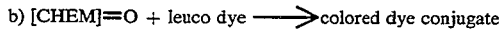
b) [CHEM]=O + leuco dye $\longrightarrow$ colored dye conjugate

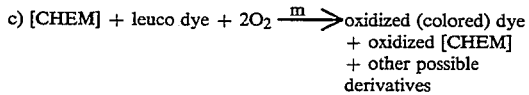
c) [CHEM] + leuco dye + 2$O_2$ $\xrightarrow{m}$ oxidized (colored) dye
+ oxidized [CHEM]
+ other possible
derivatives In reaction (a) above, the [CHEM]=O may be an epoxide or an aldehyde, or equivalent intermediate capable of conjugation with the leuco dye. Examples of such compounds include benzo(a)pyrene and formaldehyde. Alkylating agents, regardless of the presence or absence of an oxygenated functional group such as the ones generated in reaction (a), can react with the leuco dye as in reaction (b) to give a colored dye conjugate. Examples of such compounds include iodoacetic acid, among others. Chemical substances which destabilize membrane lipids in microsomes, thereby facilitating the liberation of malonaldehyde (O=CH—$CH_2$—CHO), drive reactions (a) and (b) indirectly, and are thus detected. Examples of such compounds include $H_2O_2$, or heavy metals such as Cr(VI), Cd(II), Cu(II), nickel, among others. Freshly prepared lipids, such as bovine brain lecithins, do not trigger the colored dye conjugate of reactions (a) and/or (b); however, oxidized (e.g., aged or yellowed) lipids, as well as rancid oils, do trigger the reactions. In reaction (c), the hazardous or carcinogenic [CHEM] elicits dye color by an oxidation reaction with $O_2$, which may proceed through free radical or semiquinone type intermediates. Examples of such compounds include menadione, phenol, and hydrazine. It is conceivable, even likely, that many of the chemical substances which are known or believed to form dye color through reactions (a) and (b), can also act through reaction (c). Examples may include formaldehyde and malonaldehyde generators as described above, among other compounds. All of the above mechanisms give the same overall effect.

The basic limits of the concentration of the dyestuff are determined mainly by practical considerations, the lowest level being that at which its color intensity, if colored in its reduced state, is no longer readily visible, while the upper limit would be that amount imparting such deep color density as to make discrimination of any color change difficult. In general, the dye concentration can range from about 0.2–20 mg/mL of the liquid binder medium provided that the natural coloration of the dye salt is sufficiently intense at the selected concentration as to provide sufficient contrast. Preferably, a dye concentration of about 2 mg/mL is selected to insure reasonably strong contrast and thereby facilitate unmistakable discrimination of a characteristic color change.

A collateral discovery flowing from this invention is the capacity of the reduced dye precursor oxidizable to a distinct coloration, e.g., the diphenyl- and triphenylmethane dye precursors in their reduced state, to provide a direct colorimetric indication of epoxidized organic compounds generally and not merely for the epoxidized metabolic intermediates resulting from the metabolic activity of the microsomes. This capacity is demonstrated in a subsequent working example. Therefore, reduced dye precursors are useful for the direct detection of epoxide-containing organic chemicals as such independently of the biologically active component and the NADPH. As recognized in the prior art, the detection of epoxy type organic compounds, particularly ethylene oxide and propylene oxide, is advantageous for the protection of workers in production facilities utilizing these compounds for the production of various chemical compounds, especially surface active agents. Similarly, alkylating agents such as iodoacetic acid or chloromethyldivinylbenzenestyrene polymer, or the like, react with the leuco dye to give colored products.

Although it is preferred to incorporate a colorimetric indicator into a detection element according to the invention either as a component of the same binder layer which contains the biologically active component and the NADPH or as a separate layer in contact therewith, colorimetric development of the metabolically produced intermediates could certainly be accomplished in other ways. Thus, the biologically active combination could be contained in one layer or film physically separate from a second layer or film containing the colorimetric indicator with the latter being subsequently brought into contact with the exposed biologically active film or layer to achieve oxidation of the dye precursor to its characteristically colored end state. As another alternative, it should be readily possible to develop an exposed biologically active film or layer by the application thereto of a solution of the reduced dye precursor as a thin liquid stratum whereupon the dye precursor undergoes oxidation to its distinctively colored state. The order or positioning of separate layers of dye precursor and biologically active films with respect to the exposure medium is not important, nor do both layers need to be present during an exposure step as either can be applied to the other subsequent to the exposure.

Reference has already been made to the property of benzo(a)pyrene of exhibiting after metabolic conversion by means of the metabolically active combination, e.g., microsomes plus NADPH, a fluorescence of a wavelength different from its original wavelength of fluorescence. Obviously, for actual or suspected carcinogenic compounds which exhibit different wavelengths of fluorescence in their metabolic intermediate states and the original untreated state, this affords an alternative route for determining the carcinogenic or mutagenic activity of such compounds. Other techniques for revealing the presence of metabolic intermediates of the test chemicals following exposure thereof to the metabolic active combination, e.g., microsomes and NADPH, suspended in the hydrophilic film-forming binder film will undoubtedly occur to those skilled in the art and could serve for purposes of this invention.

For most purposes, a support or carrier substrate should be provided for the films or layers of the hydrophilic film forming binder containing the metabolically active component and NADPH and/or the chemically reduced dye precursor where the latter is incorporated. Under most circumstances, the binder layer or film alone lacks sufficient structural integrity in itself as to have practical durability. Any support or carrier substrate can be used which is inert with respect to the active components or each film or layer thereon. Exemplary supports include glass, transparent polyvinylidene chloride forms sold under the trade name "SARAN WRAP," as well as sheets of films of cellulose acetate, polyester, such as "MYLAR" and the like. Additionally, plastic tissue culture dishes, e.g., polystyrene, and the like are excellent supports. Plastic, e.g., polycarbonate, ELISA well plates have also been successfully employed in the present invention. Such supports contribute sufficient structural strength and durability and facilitate handling. Uncoated paper sheets have been found unsuitable, but paper coated with plastic or possibly even with gelatin should prove acceptable.

The film or layers of the hydrophilic film-forming binder containing the appropriate other ingredients can be disposed on such support in two ways. As already alluded to, the reduced dye precursor, on the one hand, and the combination of metabolically active compound and NADPH, on the other hand, can be applied as separate films or layers, one superimposed upon the other to form a bilayer sandwich, or all ingredients can be incorporated into a common film-forming medium to form a monolayer film. Generally, it is desirable from a mechanical standpoint to add the reduced dye precursor solution and the microsome suspension into a solution of the film-forming binder and not vice-versa. For the monolayer embodiment, the reduced dye precursor should be added to the film-forming medium first, followed by the other ingredients in any order. For the dual-layer embodiment, the NADPH and the metabolically active component can be added in any order to one quantity of the film-forming medium so that both are present in a common film-forming medium. The reduced dye precursor is added to another quantity of the film-forming medium to which an additional amount of NADPH could be provided so long as an excess of NADPH is avoided. However, no real advantage is perceived in having the NADPH present in both layers other than to possibly inhibit against spontaneous oxidation of the dye precursor because of reducing action. In fact, the NADPH could conceivably serve to reduce the dye directly to its precursor state, although reliance upon a strong inorganic reducing agent is probably better.

The film-forming medium can be deposited upon the substrate in any convenient way such as by manual flowing or more preferably by spin coating in which the substrate is mounted on the axis of a spinning turntable so that, upon the deposition of an amount of film-forming medium thereto, the medium is spread quickly by centrifugal force under fairly controlled conditions. It is not necessary that the support be coated over its entirety with the film or layer system of the invention; in fact, it is preferred to confine the film to a localized, e.g., spot-like area, in order to conserve on the consumption of the microsomes or other metabolically active component. For larger scale production, any of the known coating techniques in the photographic field could be employed including so-called "curtain coating" which has now been developed to quite a refined degree for the application to moving supports of thin films or layers of such coating media as gelatin and polymer solutions. Again, in order to conserve the metabolically active component, such production coated materials could be subdivided into small sections or spots and mounted upon some other support or carrier. Film areas on the order of about 1–2 cm or so in diameter to provide a sufficient surface area that any color change therein is readily apparent.

The thickness of the layer or film of the film-forming binder as well as the area covered by a given amount of the same is mainly dependent upon the concentration of the binder, e.g., gelatin, in the binder medium and to a lesser extent by the drying conditions and the mode of coating selected. Using 2.0 mg/mL of either bovine or porcine gelatin, spots with thickness of 0.013–0.025 mm and an area of about 100–200 mm$^2$ were typical. Generally, gelatin concentrations of about 1–10% by weight will give useful binder media.

More sophisticated detection systems can be constructed if desired. For example, one area of the spot might carry a film spot containing only the reduced dye precursor as a direct indicator for exposure to epoxide-containing compounds; while another area might carry a film spot of the preferred combination of the invention including the biologically active component plus the NADPH as well as the reduced dye precursor, to give an indication of exposure to carcinogenic substances. Further, it is known that the activity of the metabolically active component, e.g., microsomes, can be induced by the administration to the laboratory animal, from which the biologically active component is to be derived, of specific chemical substances to be tested. By such induction, the ultimately derived metabolically active component, e.g., microsomes, will exhibit an enhanced activity for the administered test chemical. Consequently, additional film spots could be applied to a given support containing one or more metabolically active components having corresponding enhanced specificities for certain selected test chemicals.

An inherent property of the metabolically active component is a residual epoxide hydrolase activity which tends to inhibit the mixed function oxidation activity of the same with respect to formation of epoxide intermediates. Fortunately, such epoxide hydratase activity is short-lived, and dissipates within two hours after preparation of the component, e.g., microsomes. Thus, by simply "aging" the component for this period of time, this complication is eliminated.

Moisture is an essential condition for the realization of the mixed function oxidation activity of the metabolically active component and moisture must, therefore be provided in order to "activate" such activity. For this purpose, a detection element embodying the concept of the invention with or without the incorporated dye precursor needs to be in a moist condition during the period of exposure for the test chemical. In most cases, endogenous residual moisture from the initial preparation of the detection element is sufficient. Otherwise, pre-moistening can be achieved by the simple immersion of the element into water which allows the hydrophilic binder to imbibe sufficient water to carry out the mixed function oxidation activity, but water could obviously be applied in other ways such as by spraying or misting. However, wetting of the element with water is preferred to insure proper performance.

The NADPH tends to have a relatively short shelf life in the presence of moisture, generally lasting three days or so unless frozen, which extends the shelf life up to several months. Under refrigeration conditions, NADPH in the presence of water remains effective for only about one day. A film spot that becomes "over aged" can be identified by a pink coloration. However, an "aged" film spot can be "recharged" under some conditions by applying thereto a fresh solution of NADPH in water which restores the same to useful condition. A film spot which has not been wet with water can be stored at freezing temperatures indefinitely and at room temperature for at least several days and still exhibit its desirable activity after undergoing pre-moistening if needed.

One readily perceives that the concept of the present invention leads itself to diverse utilities. First, it becomes possible to screen new and old chemical compounds for real or suspected carcinogenic activity or other related toxic effects in a simple, relatively inexpensive and fast procedure, the results of which are available within a short time, say 10 minutes to 4 hours, and persists for a substantial period of time. Second, individuals in the work place can be equipped with personal detection elements, e.g., in the form of a film badge or strip carrying one or more of the film spots of the invention, which affords an ongoing indication of the possible exposure of each individual to hazardous substances. Alternatively, a given production facility could be equipped with a detection system embodying the invention as a permanent fixture, with the detection element being replaced every day or so with a fresh element, and in order to monitor the environmental conditions at their facility. In addition, film strips of the invention can be used to test for contamination or end of use life of protective gear. Film strips of the invention can likewise be used for leak detection in the shipment of chemical materials. Used off line, film strips of the invention can also serve to indicate spoilage or degradation of quality in foodstuffs and beverages. No doubt other purposes will occur to those skilled in the art.

The scope or range of application of the inventive concept in terms of the kinds of test chemicals that can be evaluated is, like the Ames test, believed to be quite extensive. The polyaromatic compounds, e.g., including one or more condensed ring systems, are particularly susceptible to mixed function oxidation activity, but the presence of polyaromatic nuclei is by no means an essential requirement because a variety of chemical substances lacking such nuclei can likewise be readily detected in accordance with the present invention. Nitrogen compounds, many of which are strongly mutagenic or carcinogenic, may be detectable as well. So might polyvalent metal salts which stimulate lipid peroxidation in microsomal membranes, and thereby trigger mutagenic or carcinogenic activities. The operative scope of the inventive concept is illustrated by the variety of chemicals tested in a screening tests described in the working examples (Example 5, which sampled only a few test chemicals without attempting to demonstrate the full scope of the invention; and Example 7, which sampled a statistically significant and fairly representative group of over 100-130 test chemicals).

The relationship between environmental concentration of a suspect chemical agent and its detection response by the present invention is determined by a combination of dose delivery, bioavail-ability and metabolism, and the reactivity with the leuco-dye, as shown in the following scheme.

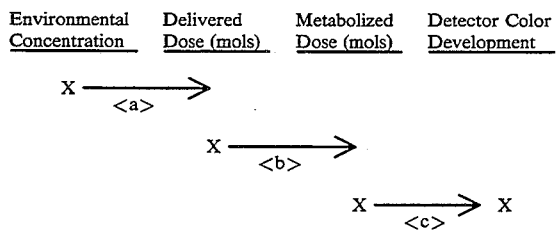

Step $<a>$ is the best understood and most thoroughly studied in environmental monitoring. The effects of steps $<b>$ and $<c>$ are conventionally accounted for separately in health effects evaluations, such as those which form the criteria for occupational standards recommended by the American Conference of Government Industrial Hygienists (conventionally referred to as threshold limit values or "TLV's") or the National Institute for Occupational Safety and Health, or risk assessment protocols. The present invention offers a potential method to measure all three steps of the above scheme.

The chemical delivery rate (CDr) is related to environmental concentration and flow rate (Vr), after correction for wall deposition artifacts and the like. An additional correction may be necessary for aerodynamic effects on chemical deposition at the target, which ordinarily is the detection element. The toxicity of an environmental/occupational chemical exposure is related to some combination of steps $<b>$ and $<c>$. Example 11, below, demonstrates the direct measurement of delivered dose, metabolized dose, and color development reactions independently for a single detector element exposure. Thus, exposure and toxicity effects can be resolved experimentally. An actual "toxicity index" related to detection element color intensity is therefore possible, in principle. Color development of detection elements following airborne chemical exposures are ordinarily determined colorimetrically as a function of CDr. Validation of the measurements consists of corroborating analyses, carried out as off-line determinations of test chemical extracts trapped at the target, e.g., the detection element of the present invention, bypassing the intermediate steps <b> and <c> of the above scheme. However, for certain types of chemical exposures, autopsy measurements on exposed detection elements serve to determine directly the initial loading and metabolic conversions of test chemical agents, and the conversions are then quantitatively compared to color development, as described in Example 11 below.

Ultimate use of the present invention is envisioned to include a calibration film strip for user reading. Calibration film strips may consist of detection elements pre-exposed to give a known color intensity and/or optical density, or alternatively, a photographic step tablet showing a color intensity gradient. The latter method is preferred by virtue of its well known color stability, provided that the coloration of the respective steps accurately simulates the detection element response over the operating range of visual intensity, as exemplified in Example 6.

Example 5 describes a validation test of the invention for carcinogen detection with fifteen chemical substances, the results being shown in Table 5. A concordance/accuracy value of 67-73% (subject to certain literature uncertainties) is calculated for detector response with respect to carcinogenic activity, from the Table 5 data. This is realistically as high an accuracy/concordance percentage as can reasonably be expected for any method (see below.). Mutagenic activity was not compared in the example. Additional experimental work, given in Example 7, confirms the results and conclusions established in this example, at a suitable level of confidence.

Example 6 describes a validation test for visual color intensity reading of detection elements, relative to optical density measurements determined spectrophotometrically. These results are included because subsequent tests of detection element response to chemical agents employed combinations of both types of methods. In the course of experimental work, variations in optics design of different spectrophotometers were found to significantly influence the measurement however, visual readings were generally consistent within the determined error range, regardless of the geographic locations or the skill levels of the observers.

Example 7 describes a concordance test (i.e., accuracy evaluation) of detection element response with respect to carcinogenic, mutagenic, teratogenic, and overall toxic activities of chemical agents. In this test, some 131 chemical substances (108 pure compounds, plus 23 commercial grade pesticide formulations) were evaluated. While this sample size is a small percentage of the 50,000+ compounds in commercial use today, it is sufficiently large to serve as a representative sample for assessing concordance/accuracy of the detection element, if the chemical compounds selected for testing are, indeed, a representative population. Two tests for representativeness are described: (1) Adequacy of representation among families of chemical substances classified according to their mechanisms of carcinogenesis or mutagenesis, and the concordance percentage of the (n=131) test compound group for the Ames mutagenicity test with respect to carcinogenicity compared to the concordance percentage for all compounds evaluated to date. The test compound group passes both tests. Among the compounds in the test group were a few which can react directly with the indicator dye. Specific examples included formaldehyde (an aldehyde), iodoacetate (a direct alkylating agent), dichromate and hydrogen peroxide (both, oxidants). Direct epoxide reaction is currently shown in Example 2 above. Microsomal oxidations catalyzed by cytochrome P450 systems generate the same types of functional groups. Microsomal reaction products not known to react directly in the present invention presently include sulfoxide intermediates and reducive dehalogenation intermediates. Intermediates in microsomal oxidarive processes involving N-functional groups apparently are detected by the present invention (e.g., hydrazines). Indirect mechanisms, particularly those involving lipid peroxidation, are inferred for polyvalent metal ions and related inorganics.

Example 7 continues with the actual concordance evaluations, the final data being presented as sets of "truth tables." The qualitative "yes"/"no" nature of the data was deemed the most appropriate form of presentation, because the substantial protocol differences in the toxic effects studies preclude quantitative comparisons. Example 7 concludes with a discussion of error factors, which points out that the observed 70% ($+/-10\%$) concordance/accuracy percentage for detector element response versus carcinogenicity approaches the upper limit of what one could reasonably expect for any detection method.

Example 8 addresses the question of which monooxygenase enzymes carry out the essential metabolic activation reactions, or produce the required metabolic intermediates for detection element response. At least 71 different cytochrome P450 isozymes have been mapped to date. One group alone (P450IA1 and P450IA2) has been specifically linked with environmental carcinogenesis and related toxic effects. The P450IA2 and P450IIC isozymes are constitutive and react with a broad range of environmental chemicals, and are therefore present in tissues from unexposed animal sources. The P450IA1 isozyme, although normally absent from unexposed tissues, is inducible by a host of environmental chemical agents. The shifted dose-response curves in Example 8 for hydrazine, a potent inorganic carcinogen but a poor mutagen in the Ames test, demonstrate metabolic activation by the P450IA and P450IIC groups, which are detected by the present invention. Other P450 isozyme reactions may be detected in similar manner, but such extrapolation is speculative at this point, as studies with specifically induced P450III and P450IV isozyme families have not yet been performed; however, such systems are not desired for the purpose of detecting carcinogenic or otherwise toxic chemical agents.

For the purpose of screening dyestuffs as candidates for the broad spectrum detection of carcinogenic or similarly toxic chemical substances in environmental media, a color development test of detection elements prepared as in Table 2 above, to hydrazine exposure, is particularly appropriate. Hydrazine, with $E_{m7}=-0.73$ V, is a very strong overall reducing agent, besides being a potent carcinogen and an acutely toxic substance. Color development related to an oxidative process in this environment surely indicates a reaction significantly focused toward the principal toxification mechanisms of the substance. The classes of leuco-dyes which react in a sufficiently consistent fashion to detect the principal toxification mechanisms, under the hydrazine conditions, is limited.

Examples 8-10 compare the kinetics of color development in indicating reactions for the present invention with NADPH redox changes, in response to exposures to hydrazine and chloromethyl methyl ether, respectively. While both carcinogens elicit positive color development, the NADPH redox changes proceed in opposite directions for the two agents. Color development response, with the present inventive leuco-dye systems, correlates with known toxic effects for hydrazine.

The best mode of the present invention is described in detail in Examples 10 and 11. In Example 10, preparation of the detection elements of the present invention, and a method of use in air monitoring under controlled laboratory conditions, are described. A second best mode of the invention, in which its use is described in monitoring personal protective gear for chemical contamination under controlled laboratory conditions, is given in Example 11. Working examples of actual use, under field conditions, of detection elements of the present invention for the air monitoring and protective gear applications are described in Examples 13 and 12, respectively.

Example 14 describes the preparation and activity of a synthetic material which is believed to possess many of the essential properties of NADPH-cytochrome P-450 reductase, and thus which might function as a synthetic analog of the reductase in the present invention.

EXAMPLE 1

Comparative Color Development of Various Constituents

In order to establish the color development behavior of various constituents employed in the invention alone and in several combinations, including two selected test chemicals, seven separate bi-layer film spots were prepared using an otherwise similar gelatin binder medium. The bottom layer of these spots contained reduced pararosaniline (PRA) in all instances except sample 7 wherein the oxidized PRA was substituted to illustrate the coloration of that constituent. An ascorbate salt was selected as typical of a benign test chemical, while benzo(a)pyrene was selected as a representative known carcinogen. The color behavior of the various samples was observed and identified in the following Table 3 together with the compositions of the samples tested.

TABLE 3

Colorimetric Reactions of Various Combinations of Constituents in Bi-Layer Film

| Layer Ingredients Present | Sample Number: | | | | | | |
|---|---|---|---|---|---|---|---|
| | 1 | 2 | 3 | 4 | 5 | 6 | 7 |
| Top Layer: | | | | | | | |

TABLE 3-continued

Colorimetric Reactions of Various Combinations of Constituents in Bi-Layer Film

| Layer Ingredients Present | Sample Number: | | | | | | |
|---|---|---|---|---|---|---|---|
| | 1 | 2 | 3 | 4 | 5 | 6 | 7 |
| Rat Liver Microsomes | Yes | No | Yes | Yes | No | No | No |
| NADPH | No | Yes | Yes | Yes | No | No | No |
| Ascorbate* | No | No | No | No | No | Yes | No |
| Benzo(a)pyrene | No | No | No | Yes | Yes | No | No |
| Bottom Layer: | | | | | | | |
| PRA-oxidized | No | No | No | No | No | No | Yes |
| PRA-reduced | Yes | Yes | Yes | Yes | Yes | Yes | No |
| COLOR REACTION: | No | No | No | Yes | No | No | Yes |

*If replaced by free ascorbic acid, color reaction occurs

EXAMPLE 2

Colorimetric Detection of Epoxide Compounds Generally

Gelatin solutions, either 100 mg/mL of 300 Bloom porcine skin or 100 mg/mL 60 Bloom bovine skin in water, containing the desired amount of pararosaniline, i.e., 0.4 mg/mL, were poured as 0.05 mL spots onto glass slides affixed to a turntable rotating at an angular velocity of 0.419 sec$^{-1}$, and air dried. Spots containing pararosaniline (PRA) were, as desired, chemically reduced by addition of approximately 10 mg of sodium metabisulfite prior to drying. To portions of these spots after drying was added a drop of an epoxy-terminated resin intermediate, i.e., the "epoxy" component of a commercial two-part (resin/hardener) epoxy resin composition. Color development results are shown in Table 4.

TABLE 4

| Ingredients/ Color Present | A | B | C | D | E | F |
|---|---|---|---|---|---|---|
| Gelatin: | Porcine | Porcine | Porcine | Bovine | Bovine | Bovine |
| PRA: | None | Oxidized | Reduced | None | Oxidized | Reduced |
| Epoxy: | None | None | Added | None | None | Added |
| INITIAL COLOR: | Clear | Magenta | Clear | Clear | Magenta | Clear |
| NEW COLOR: | None | None | Purple* | None | None | Purple |

*The purple color, which was distinct from the magenta color of the oxidized PRA, formed slowly over a period of several minutes, and remained stable for over four months.

EXAMPLE 3

Detection of Benzo(a)pyrene

Two spots were prepared by manual streaking on a glass plate. The bottom layer of each spot consisted of 0.15 mL of a 4 mg/mL porcine 300 Bloom gelatin solution containing 1.2 mg/mL pararosaniline (PRA) reduced with solid sodium metabisulfite, spread over an area of 1100-1500 mm$^2$. After drying in air for two hours, the second layer, containing the following materials, was deposited. 0.05 mL of fresh rat liver microsomes containing approximately 62 mg/mL protein was added to 0.30 mL of a sodium phosphate buffer solution (pH=7.4) containing 4 mg/mL porcine 300 Bloom gelatin, and admixed with 0.02 mL of a solution containing 3 mM MgCl$_2$, 50 mM tris(hydroxymethyl)aminomethane buffer (pH=7.4) and 15 mM KCl. To this solution was added 10.5 mg solid reduced nicotinamide adenine dinucleotide phosphate (NADPH). 0.25 mL of this material was deposited over an area of 1300-1700 mm$^2$, completely covering the bottom layer, and was air dried for two hours. Subsequently, 0.05 mL of a 0.5 mg/mL solution of benzo(a)pyrene was applied to one of the spots. Within less than five minutes, violet color began to appear, and was well developed within twenty minutes. The untreated spot, to which no benzo(a)pyrene had been added, remained transparent and clear, with no apparent violet color.

EXAMPLE 4

Activity of Microsome-Containing Layers After Four Day Time Lapse

At least five spots were prepared on a glass plate according to the procedure in Example 2 above, and dried in air. The spots were translucent but generally colorless during the first day. On the second day, one of the four spots was exposed by streaking with a benzo(a)pyrene solution, in the same manner as in Example 2. A strong violet color developed over one-half of the exposed spot, and a weaker violet color over the remainder of the exposed area. The unexposed area of the spot not streaked with benzo(a)pyrene did not change color. On the third day, two of the remaining spots were "recharged" by a new layer containing fresh NADPH in gelatin. After drying, both spots were essentially colorless. When one of these spots was subsequently streaked on that day with benzo(a)pyrene solution, the spot within minutes turned to a deep purple color. On the fourth day, the second NADPH-recharged spot was streaked with benzo(a)pyrene, and a strong violet color was elicited. An additional spot which had not been "recharged" with a fresh NADPH layer was also streaked with benzo(a)pyrene at this time and a strong violet color likewise resulted. Thus, the oxidative activity of microsomes dispersed in gelatin layers persists strongly for at least three days.

EXAMPLE 5

Screening Results with Various Test Chemicals

Detection elements prepared in a manner similar to those in Examples 3 and 4 were used for screening the carcinogenic or activity of some fourteen different chemical substances of widely differing chemical character. The results obtained with the invention, wherein the development of coloration denoted a positive response; whereas, the absence of such coloration denoted a negative response, were observed and the results thereof summarized in the following Table 5 together with the known carcinogenic status of the test compounds in question as reported in the literature. Exposure of the element, i.e, film spot to the test chemical varied according to the state of that chemical. When the test chemical was solid, it was applied in powder form sprinkled sparsely over the test spot, and in that case, a positive response tended to appear in localized spots corresponding to the particles of the test chemical, although in some instances where the test chemical appeared to be readily soluble in the moistened binder, e.g., phenol, the coloration developed over the entire area. Where the test chemical was in vapor form, the test spot was exposed to vapor by holding the same a short distance away from a container of the test chemical. In the case of chlordane, an element carrying a detector spot of the invention was placed perhaps twenty feet distant from a neighboring site to which a chlordane-containing pesticide was being applied. It will be observed that the response results given by the invention correspond closely with known carcinogenic status of the chemicals tested.

TABLE 5

Initial Screening Results of Various Test Chemicals by Invention Versus Known Carcinogenic Status

| Test Chemical Substances | Carcinogenic Status[1] | Invention Response |
| --- | --- | --- |
| Benzo(a)pyrene (all forms) | Positive | Positive |
| Aniline (vapor) | Possible[2] | Positive |
| Chlordane (vapor) | Positive | Positive |
| Formaldehyde (solution) | Probable[3] | Positive |
| DCMU (solid)[4] | Teratogen only | Positive |
| MNNG (solid)[5] | Positive | Negative |
| Menadione (solid) | Possible | Positive |
| Coumarin (solid) | Positive | Positive |
| Tetramethylurea (liquid) | Possible/ Teratogen | Positive? |
| Phenol (solid or solution) | Possible[6] | Positive |
| POPOP (solid)[7] | Negative | Negative |
| Acetate (solid or solution) | Negative | Negative |
| Ascorbate (solution)[8] | Negative | Negative |
| Sucrose (solution) | Negative | Negative |
| Styrene (vapor) | Negative | Negative |

[1]Status reported by Lewis and Tatken, "1979 Registry of Toxic Effects of Chemical Substances," DHHS(NIOSH) Publication No. 80-111, U.S. Department of Health and Human Services: Cincinnati, OH, September 1980; and by Lewis and Sweet, "1983–84 Cumulative Supplement, Registry of Toxic Effects of Chemical Substances," DHHS(NIOSH) Publication No. 86-103, U.S. Department of Health and Human Services: Cincinnati, OH, November 1985.
[2]Highly toxic, irrespective of carcinogenicity.
[3]Negative in most carcinogenicity tests, but reportedly positive in some studies.
[4]3-(3,4-Dichlorophenyl)-1,1,dimethylurea, a commercial herbicide.
[5]N-Methyl-N'nitro-N-nitrosoguanidine.
[6]Negative in most carcinogencity tests, but reportedly positive in some studies.
[7]p-bis[2-(4-phenoxyazolyl)]-benzene.
[8]Positive response observed under strongly acidic conditions.

EXAMPLE 6

Visual Intensity Validation Test

Figure 2:
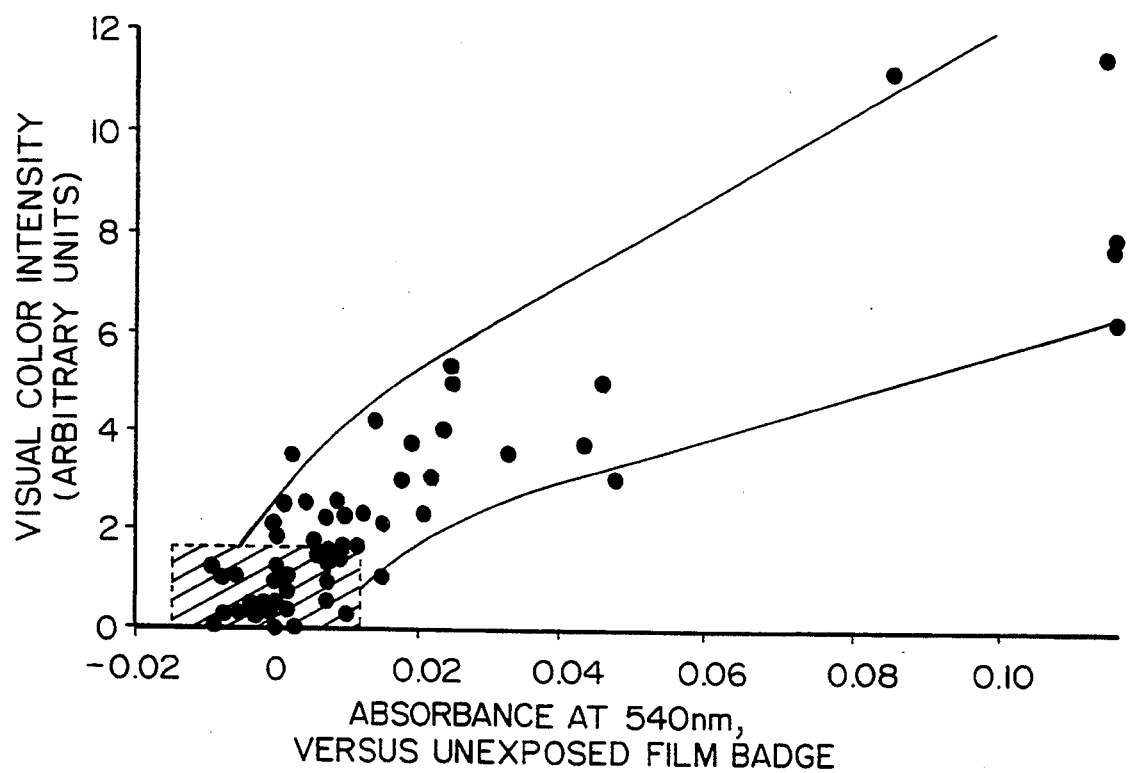
FIG. 2 is a plot of data obtained in Example 6, showing a correlation, for detection elements according to the present invention, of visual color intensity versus optical density of the elements.

Detection elements prepared in a manner similar to those of Examples 3–5 were applied to a plastic transparency sheet in nine rows of eight units. These were treated with chemical agents, in order to elicit color development of varying intensities, which were then read by four individual evaluators and compared with visible absorption spectra. Detection elements were scored by the evaluators on a scale of "0–10" using four "0" blanks and six "10" standards for reference. Each detection element unit was then 10 affixed to the exit slit of the sample path in a double-beam spectrophotometer, and its spectrum recorded against an unexposed unit in the reference path. Twenty-five of the 72 detection elements were unexposed controls. FIG. 2 shows the mean of the four scores for each detection element plotted as a function of the dye absorbance determined spectrophotometrically. Visible spectra were recorded against a blank detection element, which contained 0.013 mM oxidized dye. Curves represent the 95% confidence limits of the data points. Shaded area represents the 95% confidence region (both axes) for the unexposed controls. As FIG. 2 shows, for example, a visual reading of "4" corresponds to an optical density of 0.033+/−0.012 (0.040 mM oxidized dye); conversely, a 0.03 absorbance (0.035 mM oxidized dye) equals a visual intensity of "4.5"+/−1.0. In general, as this example shows, visual intensity readings are precise to within +/−30%, and are likewise accurate to within +/−30%. Visual acuity is most apparent near the detection threshold of color development in test strips of the present invention.

In FIG. 2, individual data points reflect the mean of the visual intensity estimates by four evaluators and the peak wavelength absorbance relative to the interpolated baseline value. Curves represent the 95% confidence limits of the data points. Shaded area represents the 95% confidence region (both axes) for the clean air controls. Visible spectra were recorded against a blank film badge, which contained 0.013 mM oxidized dye.

EXAMPLE 7

Concordance Evaluation of Detection Element

Detection elements were prepared in similar manner to those described in Examples 3-6, exposed to varying doses of test chemicals, and color development read either visually or spectrophotometrically. A total of 131 test substances were used in the evaluation (an additional 15 materials, identified by "$" in Table 6, were not included in this group), 108 pure compounds and 23 commercial grade pesticides. Selection of the test substances employed four criteria: (1) Representativeness with respect to the 50,000+ chemical compounds in commercial use; (2) Availability of information on carcinogenic and related toxic effects from the *Registry of Toxic Effects of Chemical Substances* published by the National Institute for Occupational Safety and Health (R. L. Lewis and D. V. Sweet, eds. (November 1985), DHHS (NIOSH) Publication 86-103 , Public Health Service, U.S. Department of Health and Human Services: Cincinnati, Ohio 45226; hereinafter referred to as "NIOSH RTECS"); (3) Balance—i.e., comparable numbers of non-carcinogens as carcinogens; and (4) Commercial importance and other factors. Representativeness was assessed by two independent methods.

Figure 3:
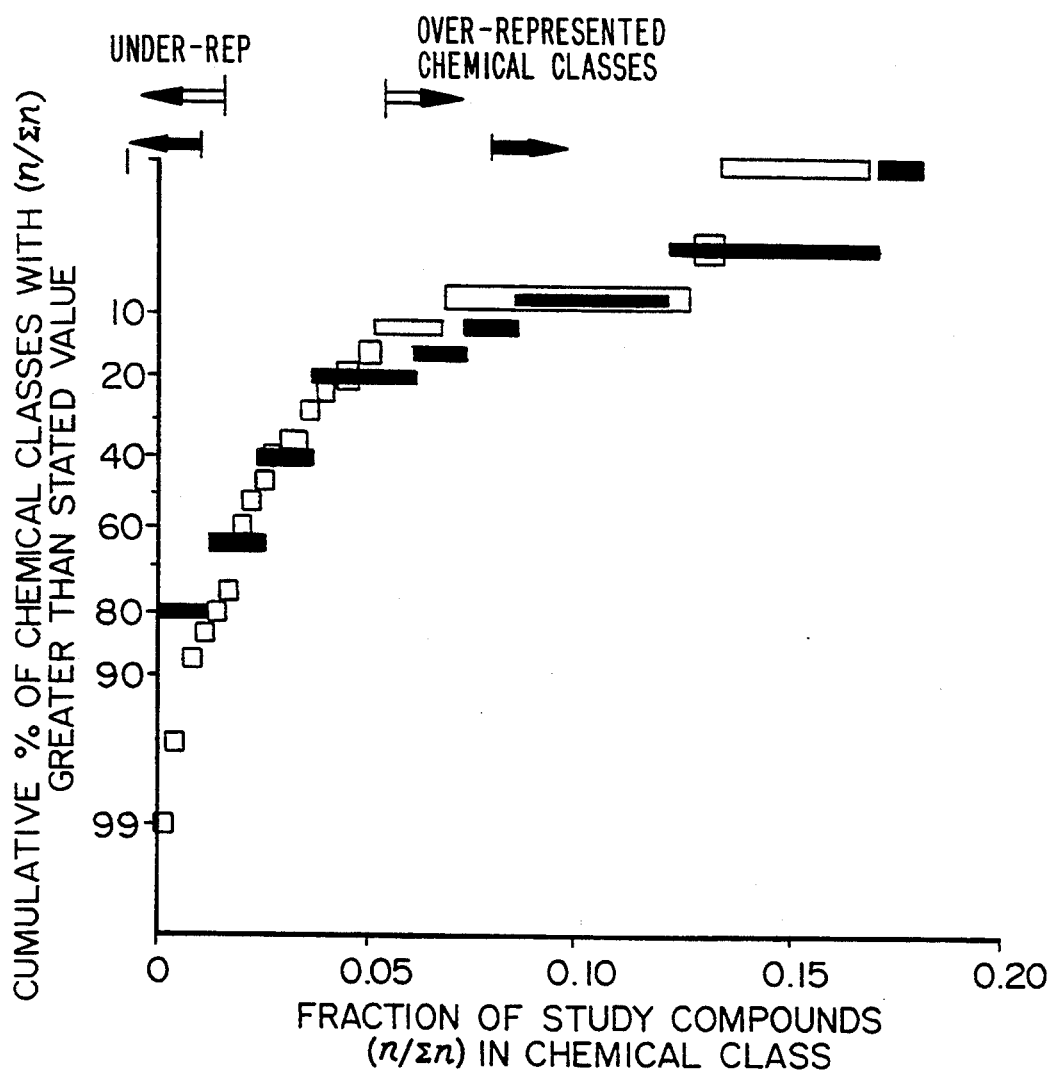
FIG. 3 is a plot of the data obtained in Example 7, showing a correlation of the response of detection elements according to the present invention with published data regarding carcinogenic and related toxic effects of 131 test compounds.

One assessment method compared the adequacy of representation in 26 identified classes (Rinkous, S. J., and M. S. Legator (1979) "Chemical Characterization of 465 Known or Suspected Carcinogens and Their Correlation with Mutagenic Activity in the *Salmonella typhimurium* System," Cancer Research, Volume 39: pages 3289-3318.) of chemical carcinogens among the chemical agents studied, specifically: triazene, diazo, azoxy, nitroso, diaryl alkynyl carbamate, aromatic amine, nitroaromatic, polyaromatic, aziridine, oxirane/-thiirane, heteroaromatic, halomethane/haloethane, N-/S-/ or O-mustard, sulfate/sulfonate/sulfone, phosphate, hydrazine, lactone, chloroethylene, inorganic, azo, carbamyl/thiocarbamyl, phenyl, benzodioxazole, polychlorinated cyclic, steroid, and antimetabolite. FIG. 3 shows the results, expressed as a percentage of the study sample, compared with the representation reported by Rinkous and Legator.

In FIG. 3, the solid symbols represent data obtained in this Example. (In the total study sample of $n=131$ compounds, $\Sigma n=82$ could be classified.) The open symbols represent data from Rinkous and Legator (1979), involving a study sample of $\Sigma n=416$ compounds. Boundaries for under-represented ("Under-Rep.") classes and "over-represented" classes of chemical compounds were determined from frequency histograms of numbers of compounds represented in each class compared to 95% confidence limits (i.e., $\pm$ two standard deviations about the mean).

Of the 26 classes, 5 were inadequately represented among the test compounds studied, and 3 are over-represented. This distribution was virtually indistinguishable from the Rinkous and Legator population. Since non-mutagenic non-carcinogens were not classified, this assessment method could only be applied to a portion ($n=82$) of the study sample. Consequently, a second assessment method was necessary to confirm representativeness. Table 6 lists the compounds presently studied.

The second assessment method compares the concordance percentage (accuracy) of an existing short-term bioassay procedure with respect to carcinogenicity for the present study sample, with that for all chemical substances evaluated to date. This comparison is a strictly statistical test. If the Ames *Salmonella*-microsome test is used, the concordance percentage over the present study sample was $66+/-2\%$ <*>, compared <*> See Table 7 for description of "truth tables."

|  | Carcinogenicity | |  |
|---|---|---|---|
| Mutagenicity | + | − |  |
| + | 29 (28) | 12 (7) | Accuracy = 67% (65%). |
| − | 33 (29) | 57 (44) |  |

TABLE 6

Chemical Response Spectrum of Detection Elements

| Candidate Chemical Substance | Detector Response[1] | Mutagen-icity[2] | Tumorigen Activity[3] | Teratogen Activity[4] |
|---|---|---|---|---|
| 1. Formaldehyde | $0.01^a$, $+^b$ | −, $+^d$ | + | + |
| 2. Dimethylformamide | $-^a$, $-^b$ | + | − | − |
| 3. Acrylonitrile | $20^a$, $-^b$ | + | + | + |
| 4. CS$_2$ | $-/+^a$, $-^b$ | + | − | + |
| 5. Acrylamide | $0.2^a$, $+^{b,f}$ | − | + | − |
| 6. Phenol | $0.02^a$, $+^b$ | $+^i$, $-^n$ | − | − |
| 7. 1,2-Dichloroethane | 20 | + | + | − |
| 8. 1,2-Dibromoethane | − | + | + | − |
| 9. CHCl$_3$ | $-/+^a$, $-^b$ | + | + | + |
| 10. Trichloroethylene | $150^a$, $-^b$ | + | + | + |
| 11. Tetrachloroethylene | − | + | + | + |
| 12. Phenoxyacetate | + | − | − | − |
| 13. 2,4-D | $+^a$, $-/+^b$ | − | $+^i$, $-^n$ | + |
| 14. 2-Chlorophenol | <1 | − | + | − |
| 15. 3-Chlorophenol | <1 | − | + | − |
| 16. 4-Chlorophenol | <1 | + | + | − |
| 17. Quinhydrone | 0.1–0.2 | − | $+^e$ | − |
| 18. Menadione | 0.01 | + | $+^e$ | + |
| 19. Anthraquinone | 1–20 | − | − | − |
| 20. Toluene | −/+ | − | − | + |
| 21. Naphthalene | − | − | $+/-^e$ | + |
| 22. Benzo(a)pyrene | 0.01 | + | + | + |
| 23. Acetone | >50 | − | − | − |
| 24. Methanol | $-^a$, $-^b$ | − | − | + |
| 25. Ethanol | $-^a$, $-^b$ | − | − | + |

TABLE 6-continued
Chemical Response Spectrum of Detection Elements

| Candidate Chemical Substance | Detector Response[1] | Mutagen-icity[2] | Tumorigen Activity[3] | Teratogen Activity[4] |
|---|---|---|---|---|
| 26. 2-Propanol | $-^a, -^b$ | − | $-, +^{i,g}$ | − |
| 27. 1-Butanol | $-/+^a, -^b$ | − | − | − |
| 28. Glycerol | − | − | − | − |
| 29. Cyanamid | 30 | + | $+^e$ | |
| 30. Hydrazine | $0.1-20^a, +^b$ | + | + | + |
| 31. NH$_2$OH | 0.1 | $-, +^d$ | − | − |
| 32. H$_2$O$_2$ | 1-2 | + | $+^i$ | − |
| 33. 2,4-Dinitro-phenylhydrazine | 0.01 | + | − | − |
| 34. Barbital | − | − | − | − |
| 35. Acetate | − | − | − | − |
| 36. Citrate | − | − | − | − |
| 37. Nitrilotriacetate | 2. | − | $+^a$ | + |
| 38. EDTA | $+/-^a, -^b$ | − | − | + |
| 39. Trichloroacetate | 3. | ? | −? | − |
| 40. Ascorbate | $-^a, -^b$ | + | $-^a$ | + |
| 41. Mannitol | − | − | $-^a$ | − |
| 42. 2-Thiourea | 7. | + | + | + |
| 43. DCMU | + | + | $+^e$ | + |
| 44. Tetramethylurea | +/− | − | − | + |
| 45. Methylnitro-nitrosoguanidine | − | + | + | + |
| 46. Diethylnitrosamine | $0.1-1^a, +^b$ | + | + | + |
| 47. Dimethylsulfoxide | − | − | − | + |
| 48. KCN | − | − | − | + |
| 49. NaN$_3$ | − | + | $+/-^e$ | − |
| 50. Cr(VI) | 0.1 | + | $+^e$ | − |
| 51. Cd(II) | 0.3, but 0.05$^h$ | + | $+^i$ | + |
| 52. Aniline | 5. | + | $+^e$ | |
| 53. Diphenylamine | 100 | − | − | + |
| 54. 8-Hydroxyquinoline | $0.3^a, +^b$ | + | + | − |
| 55. o-Phenanthroline | − | − | − | − |
| 56. Methylene(bis)-acrylamide | $<2.^a, +^b$ | − | − | − |
| 57. Diethyldithio-carbamic acid | 0.2 | − | $-^n, +^t$ | + |
| 58. Ergosterol | 0.1 | − | − | + |
| 59. Hydrocortisone | 0.1 | − | − | + |
| 60. Deoxycholate | 0.5 | − | − | + |
| 61. Methylhydro-quinone | 30. | − | − | − |
| 62. m-Cresol | 2. | − | − | − |
| 63. 2-Naphthol | 20. | − | − | − |
| 64. BHA | 0.3 | − | + | − |
| 65. Triethylamine | −/+ | − | − | − |
| 66. Sodium laurylsulfate | − | − | − | − |
| 67. Triton X-100 | − | − | − | − |
| 68. Formamide | 100 | − | − | + |
| 69. Urea | − | − | + | − |
| 70. Ethyl Acetate | − | − | − | − |
| 71. Ethyl p-Hydroxy-benzoate | 30. | − | − | + |
| 72. 5,6-Naphthoflavone | −/+ | − | − | − |
| 73. n-Hexane | − | − | − | − |
| 74. C$_{19}$H$_{40}$ | + | − | $+^e$ | − |
| 75. 1,4-Dioxane | 10. | − | $+^n$ | − |
| 76. Theophylline | − | − | − | + |
| 77. Dieldrin | $+^a, -^{b,j}$ | + | $+^e$ | + |
| 78. Lindane (USP) | $0.2^a, +^b$ | − | + | + |
| 79. Alachlor (ind.) | $+/-^a, -^b$ | − | − | − |
| 80. Malathion (ind.) | 0.1 | $-, +^d$ | − | + |
| 81. Endosulfan (ind.) | 0.1 | − | $-^n, +^b$ | + |
| 82. Diazinon (ind.) | $1-100^a, -^b$ | − | − | + |
| 83. Picloram (ind.) | $0.01^a, +^b$ | − | $+^n$ | + |
| 84. Atrazine (ind.) | $0.05^a, +^b$ | − | $+^e$ | − |
| 85. Simazine (ind.) | + | − | $+^e$ | + |
| 86. Cyanazine (ind.) | + | + | − | − |
| 87. Metolachlor (ind.) | $+/-^a, -^b$ | + | − | − |
| 88. Chlorpyrifos (ind.) | $0.01^a, +^b$ | − | − | + |
| 89. Glyphosate (ind.) | $0.3^a, +^b$ | − | − | − |
| 90. Sumicidin (ind.) | 0.5 | −? | −? | −? |
| 91. Fonfos (ind.) | $10-100^a, +b$ | − | − | − |
| 92. Isozofos (ind.) | − | −? | −? | −? |
| 93. Propoxur (ind.) | − | − | − | − |
| 94. Mexacarbate (ind.) | − | − | $-^n, +^b$ | − |
| 95. Carbofuran (ind.) | − | + | − | − |
| 96. Isofenphos (ind.) | − | − | − | − |
| 97. Methomyl (ind.) | + | − | − | − |
| 98. Paraquat (ind.) | − | + | − | + |

TABLE 6-continued

Chemical Response Spectrum of Detection Elements

| Candidate Chemical Substance | Detector Response[1] | Mutagenicity[2] | Tumorigen Activity[3] | Teratogen Activity[4] |
|---|---|---|---|---|
| 99. Tetradifon (ind.) | + | − | − | − |
| 100. Carbaryl (ind.) | + | + | + | + |
| 101. Dicamba (ind.) | + | + | − | − |
| 102. Iodoacetamide | 0.1 | − | + | − |
| 103. Aged Quartz (SiO$_2$) | − | − | + | − |
| 104. $Fresh Quartz (SiO$_2$) | + | − | − | − |
| 105. Glass (NaBSiO$_2$) | − | − | −, +$^{b,e}$ | − |
| 106. Diesel Soot | + | + | +$^e$ | − |
| 107. Coal Solids | −$^a$, +$^b$ | − | +/−$^e$ | − |
| 108. Grain Dust | − | − | − | − |
| 109. $Isoascorbate | − | ? | ? | ? |
| 110. $MOPS Buffer | − | −? | −? | −? |
| 111. p-Hydroxybiphenyl | + | − | + | −? |
| 112. Glycidoxypropyl-trimethoxysilane | +/− | − | − | − |
| 113. $1-Ethyl-3-(3-dimethylaminopropyl)-carbodiimide | +/− | ? | ? | ? |
| 114. TRIS Buffer | −$^a$, −$^b$ | − | − | − |
| 115. Raney Nickel | −, but +$^k$ | − | +$^i$ | − |
| 116. $Ni(II) | <1. | − | +$^i$, +$^{b,n}$ | + |
| 117. $Allylisopropyl-acetamide | + | ? | ? | ? |
| 118. $Chloromethyl methyl ether | 0.1 | + | + | + |
| 119. Phenylmethylsulfonyl fluoride | − | − | − | − |
| 120. $Diisopropyl-fluorophosphate | − | − | − | − |
| 121. Barium(II) | 20–100 | − | − | − |
| 122. $BaSO$_4$ Dust | −/+ | − | +/−$^e$ | − |
| 123. Calcium(II) | 10 | − | +/− | − |
| 124. Magnesium(II) | − | − | − | − |
| 125. NaCl | − | − | − | − |
| 126. KCl | − | − | − | − |
| 127. NH$_4$Cl | − | − | − | − |
| 128. Manganese(II) | 5 | − | + | + |
| 129. Copper(II) | 5 | − | +/− | + |
| 130. Dysprosium(III) | 5 | − | −$^k$ | − |
| 131. Lanthanum(III) | 5 | − | −$^k$ | − |
| 132. AgNO$_3$ | <5 | −$^m$ | +/− | − |
| 133. $Tetramethyl-benzidine | − | − | − | − |
| 134. BHT | 200 | − | +/− | − |
| 135. Lecithin, fresh | − | − | − | − |
| 136. Lecithin, oxidized | + | + | + | − |
| 137. Methyl viologen | + | + | + | + |
| 138. Cyanacrylate (ind.) | ++ | −$^k$ | − | − |
| 139. NaNO$_2$ | 0.1 | + | + | + |
| 140. NaOH | − | − | − | − |
| 141. HCl | − | − | − | − |
| 142. $Firefighters' smoke | ++ | + | + | +? |
| 143. $Pryfon (ind. grade) | + | ? | ? | ? |
| 144. $Methylene Blue (USP) | − | + | − | − |
| 145. $Ozone (0.2 ppm) | + | − | +$^b$ | + |
| 146. $Asbestos (Chrysotile) | − | − | + | − |
| 147. $Asbestos (Crocidolite) | ++ | − | + | − |
| 148. $Asbestos (Amosite) | +/− | − | + | − |

[1] Detection element response is considered positive ("+") if discernible color develops within 24 hours after exposure to a dose of <10 micromols. Numerical values represent threshold dose, in micromols. The symbol "+/−" designates a response detected at a 20–100 micromol dose. The symbol "−/+" designates a response detected at a 200–1000 micromol dose. All other responses are designated "−". The "a" and "b" superscripts indicate independent evaluations with two different rat sources for microsomal material.
[2] Mutagenic activity in the Ames Salmonella-microsome test as reported in the NIOSH RTECS ("mma-sat"). Direct-acting mutagens are designated by a "d" superscript.
[3] Carcinogenic activity is indicated by "+." Benign tumors only are designated by "+, b". Equivocal tumorigenic agents are indicated by an "e" superscript or by "+/−". Assignments based on IARC reports ("i" superscript) or NCI/NTP carcinogenesis bioassay results ("n" superscript) are shown separately, if different. Source: NIOSH RTECS, "V01...", "V02...", "V03..."
[4] Toxic effects are listed as "T35..." to "T59..." in NIOSH RTECS.
[f] Color development slow, but ultimately strong.
[g] Assignment based on industrial production, in which culpable agent is an oil impurity.
[h] Serum protein-bound Cd(II) is more potent than the free metal, triggering color development at 0.05 micromols.
[j] Negative response due to partitioning effects.
[k] Free metal, over a monitoring period of 7 days or less. However, archived film badges reveal a strong positive response at t > 2 months. (Archived blanks remained clear.)
[m] Literature (i.e., NIOSH-RTECS) designations may be subject to question, as toxic effects of related compounds all show "+".

with 59+/−5% overall (Mendelsohn, M. L. (1988) "Can Chemical Carcinogenicity Be Predicted by Short-Term Tests?" *Annals of the New York Academy of Sciences,* Volume 53: pages 115-126.). Based on these criteria, one can reasonably assume that the present test compounds were probably as representative of the whole, as any group of 100 +/−20 chemical substances which one might choose.

The Table 7 "truth tables" suggest that detection element response correlates roughly with tumorigenic activity of the 105-107 pure compounds surveyed. A more quantitative assessment covering all of the test compounds is not justified. Inclusion of the crude pesticide materials does not significantly affect the overall results. As evidenced by concordance percentages near 50%, detection element response is virtually random with respect to the Ames *Salmonella* microsome test and also to teratogenicity bioassays (Lewis and Sweet, 1986, op cit). By contrast, its response correlates with carcinogenicity much more closely, at 70+/−10% (Table 7), which is as high as existing short-term bioassays give (Mendelsohn specifically reports the following concordance percentages with carcinogenicity, for example: Ames test, 59+/−3%; chromosome aberration in hamster lung fibroblasts, 75+/−7%; sister chromatid exchange in hamster lung fibroblasts, 72+/−4%; chromosome aberrations in bone marrow in vivo, 63+/−4%; and recombination in *Bacillus subtilis,* 68+/−5%; all short-term bioassays collectively, 67+/−3%).

tion of such hazards (Ashby, J. (1988) "The Value and Limitations of Short-Term Genotoxicity Assays and the Inadequacy of Current Cancer Bioassay Chemical Selection Criteria," *Annals of the New York Academy of Sciences,* Volume 534: pages 133-138; and Purchase, I.F.H. (1988) "Short-Term Tests—Relevance for Human Cancer Risk," *Annals of the New York Academy of Sciences,* Volume 534: pages 139-140.). However, if one considers that literature assignments (NIOSH RTECS) of carcinogenicity are either equivocal or uncertain for at least 19% of the study group compounds and that marginal detection element responses were observed for at least 22% of the chemical substances, the present accuracy ratio should not come as a surprise.

The accuracy ratio for detection element response to carcinogenicity is about the same as that for carcinogenicity bioassays among themselves. Carcinogenicity assignments have been predicated on results obtained from research using a variety of animal strains and test protocols, an obvious source of uncertainty. A close examination of U.S. National Toxicology Program bioassay data (Huff, J. E., E. E. McConnell, J. K. Haseman, G. A. Boorman, S. L. Eustis, B. A. Schwetz, G. N. Rao, C. W. Jameson, L. G. Hart, and D. P. Rall (1988) "Carcinogenesis Studies, Results of 398 Experiments with 104 Chemicals from the U.S. National Toxicology Program," *Annals of the New York Academy of Sciences,* Volume 534: pages 1-30.) with rats and mice reveals a 70% concordance (accuracy) ratio between the two species for carcinogenesis. The policy of designating a

TABLE 7

Concordance "Truth Tables" for Film Badge Response

| | | Test Parameter | | |
|---|---|---|---|---|
| | | "+" | "−" | |
| Response Parameter: | "+" | True Positive (T+) | False Positive (F+) | Accuracy = $\frac{(T+) + (T-)}{(F+) + (F-) + (T+) + (T-)}$ |
| | "−" | False Negative (F−) | True Negative (T−) | |

Carcinogenicity

| | | "+" | "−" | |
|---|---|---|---|---|
| Film Badge Response: | "+" | 36-49 | 14-27 | Accuracy = 68/105 to 84/105 = 61-80%. |
| | "−" | 7-14 | 28-35 | Ac = 70%<br>Tk = 70% |

Mutagenicity

| | | "+" | "−" | |
|---|---|---|---|---|
| Film Badge Response: | "+" | 22-28 | 35-45 | Accuracy = 51/107 to 65/107 = 48-61%. |
| | "−" | 7-11 | 29-37 | Avg.: 54% |

Teratogenicity

| | | "+" | "−" | |
|---|---|---|---|---|
| Film Badge Response: | "+" | 24-32 | 34-44 | Accuracy = 48/107 to 63/107 = 45-59%. |
| | "−" | 7-15 | 24-31 | Avg.: 52% |

The present invention can serve as a carcinogenic hazard indicator. One might argue that the 70% accuracy factor (Table 7) is too low to give a credible indicasubstance which induces malignant tumors in either rat or mouse strain as a carcinogen is based on a conservative view toward protection of human populations. Extension of this policy with additional animal strains, while giving similar concordance percentages between any two, would increase the fraction of chemical substances reported as positive overall for carcinogenicity.

Individual differences within species may likewise limit concordance (accuracy). In the present example, preparations from two supply sources of Sprague-Dawley rats affected detection element response to at least one chemical agent—dioxane, and may have accounted for discordant responses to as many as 6 out of 28 compounds tested in common. This gives an apparent concordance percentage of 79%, which reflects "rat-to-rat" influences.

Individual differences in metabolic activation related to carcinogenesis among humans are reportedly substantial. According to A. H. Conney (1982) "Induction of Microsomal Enzymes by Foreign Chemicals and Carcinogenesis by Polycyclic Aromatic Hydrocarbons," *Cancer Research*, Volume 42: pages 4875–4917, benzo(a)pyrene metabolism rates in human liver or placenta, compared among different individuals, can vary over two orders of magnitude. Activities observed in Ames Salmonella-microsome bioassays using the same individual tissue sources are correspondingly varied. Although the human sample population was small (n=10–13), such a large intraspecies difference in activity levels undoubtedly propagates to individual differences in sensitivity.

The present detection element method does not mirror mutagenicity as detected in the Ames Salmonella-microsome test. Chemical classes which are detected poorly in the Ames test but which elicit strong detection element color response include, steroids, hydrazines, thiocarbamyl agents. On the other hand, the detection element exhibits relatively low sensitivity to chlorinated methanes and ethanes and ethylene solvents. As a general observation, compounds such as phenols, aldehydes, alkylating agents, quinones, hydrazines, acrylics, metals and oxidants can be counted on to elicit strong color development in the detection element.

Figure 4:
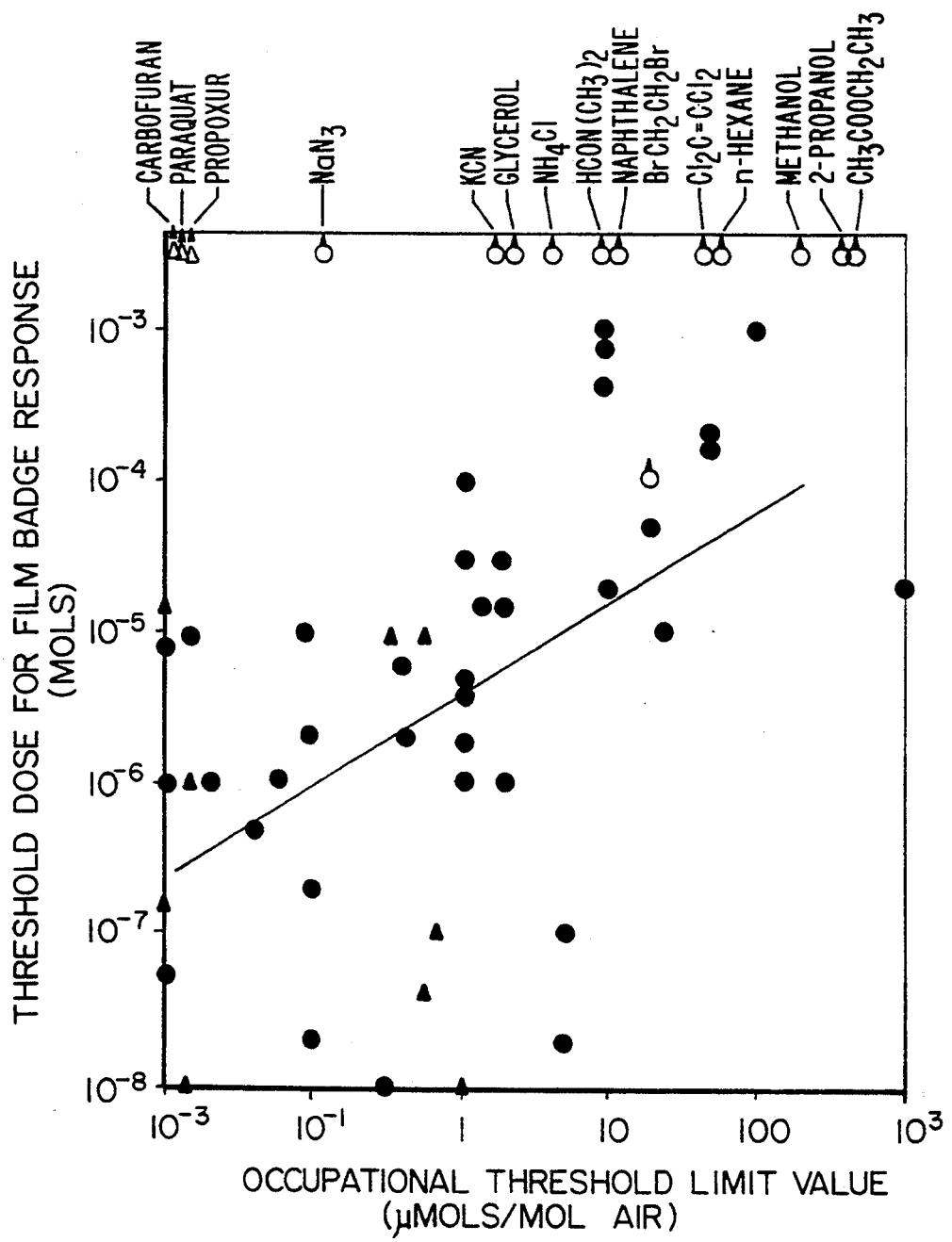
FIG. 4 is a plot of correlation data obtained in Example 7 pertaining to the sensitivity of responses of detection elements according to the present invention compared with available occupational threshold limit values ("TLVs") for the 131 compounds and substances listed in Table 6.

As a further example of the utility of the present invention for toxicity-based detection in environmental or occupational media, the response of detection elements of the present invention is compared with available occupational threshold limit values ("TLV's") among the test chemical substances described above (Table 6). FIG. 4 shows the results. Of the 131 substances in the present example, TLV's have been published for some 61 compounds (Lewis and Sweet (1986), op cit), and 45 of these elicited a positive detector element response. This suggests a 73% concordance percentage, on a strictly "yes/no" basis. A rough semi-quantitative association is observed (FIG. 4) between detector element sensitivity and the TLV, when one examines the data points in greater detail. Thus, the present invention correlates with combined (TLV criteria) toxic effects approximately at least as well as it correlates with carcinogenicity, for indicating environmental chemical hazards. When one considers the uncertainties and variabilities inherent in detector element response thresholds and the criteria upon which most of the TLV's are predicated, the level of agreement in FIG. 4 is surprisingly good. (In FIG. 4, both ordinate and abscissa scales are logarithmic. Solid symbols are chemical substances that elicit a positive biosensor response at the state threshold dose, and for which occupational TLVs have been published. The straight line represents a log-log linear regression slope, $r^2=0.26$. Open symbols represent chemicals substances (named) for which TLVs exist, but which do not elicit measurable biosensor response. Triangles represent crude pesticides. Circles represent pure agents.)

EXAMPLE 8

Evaluation of Metabolic Activating Component in Detection Element

Figure 5:
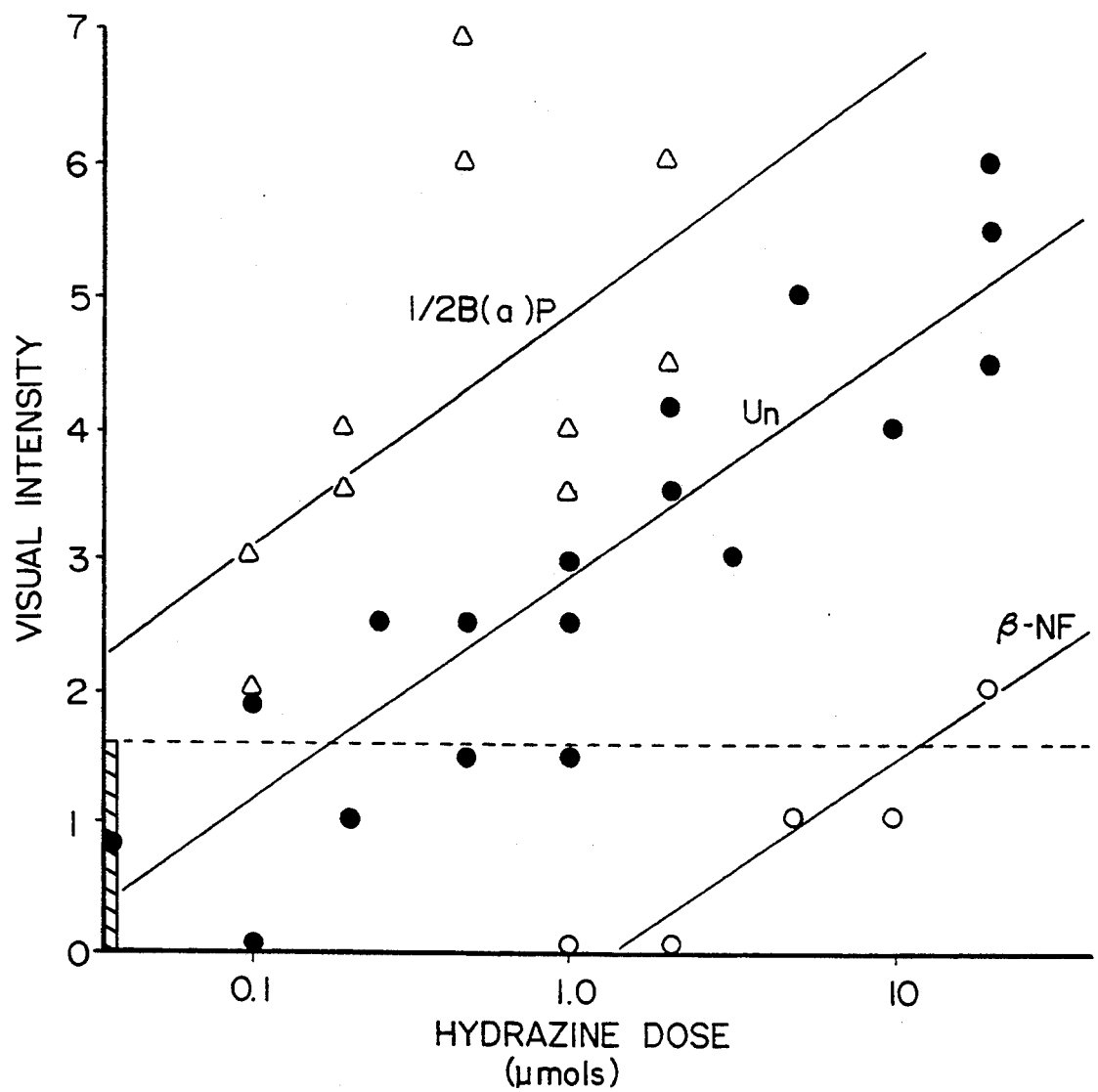
FIG. 5 is a plot of data obtained in Example 8, showing logarithmic dose-response curves of detection elements according to the present invention to hydrazine, wherein "½B(a)P" denotes detection elements containing benzo(a)pyrene-induced microsomes mixed 1:1 with uninduced microsomes; "Un" denotes detection elements containing uninduced microsomes; and "β-NF" denotes detection elements containing beta-naphthoflavone-induced microsomes.

Detection elements were prepared in similar manner to those described in Examples 3–7, with the exception that microsomal preparations in some cases were isolated from livers of rats which had been injected i.p. with either 5,6-benzoflavone (also referred to as beta-naphthoflavone, "BNF") or benzo(a)pyrene ("BaP") 24 hours prior to sacrifice. According to D. W. Nebert and F. J. Gonzalez (1987) "P450 Genes: Structure, Evolution and Regulation," *Annual Review of Biochemistry*, Volume 56: pages 945–993, both BNF and BaP are potent inducers of cytochrome P450IA1. However, according to F. J. Wiebel, J. C. Leutz, L. Diamond, and H. V. Gelboin (1971) "Aryl Hydrocarbon (Benzo[a]pyrene) Hydroxylase in Microsomes from Rat Tissues: Differential Inhibition and Stimulation by Benzoflavones and Organic Solvents," *Archives of Biochemistry and Biophysics*, Volume 144: pages 78–86, BNF also strongly inhibits the catalytic activity of P450IA1. FIG. 5 shows logarithmic dose-response curves of detection elements to the inorganic carcinogen hydrazine ($H_2N$—$NH_2$). Detection elements prepared with BNF-induced microsomes are a factor of 20–50 fold less sensitive to hydrazine exposure than are comparable detection elements prepared with microsomes from "naive" uninduced rats. By contrast, detection elements prepared with a 50%:50% mixture of BaP-induced microsomes and uninduced microsomes give approximately 10-fold more sensitive response than do uninduced control elements (FIG. 5). Since BNF inhibits only the cytochrome P450IA1 mediated activity, the sensitivity shifts observed in FIG. 5 clearly demonstrate the P450IA family of monooxygenases as the responsible metabolic activating agents for hydrazine. Parallel tests comparing BNF-induced detection elements with uninduced controls show similar dose-response shifts with BaP, acrylonitrile, and p-dioxane; but less significantly with trichloroethylene, phenol, or cadmium. (In FIG. 5, solid circles represent uninduced microsomes; open circles represent BNF-induced ($\beta$-NF-induced) microsomes; and triangles represent BaP-induced microsomes mixed 1:1 with uninduced microsomes. The shaded bar with dashed horizontal line represents the range of visual intensity observed for unexposed blank detection elements (FIG. 2 ).)

The FIG. 5 dose-response shifts accurately reflect the range of metabolic activation rates as reported by Conney (1982) op cit; and thus, one can infer measurement by the present invention of different sensitivities of human sub-populations to environmental chemical agents. In this respect, detection elements with microsomal preparations from induced tissue sources, as well as uninduced sources, are useful as simulators of different risk groups. For example, detection elements prepared with benzo(a)pyrene induced microsomes can serve as chemical hazard indicators for high-risk individuals (e.g., heavy cigarette smokers). Conversely, detection elements with flavone-induced preparations might be useful as an environmental hazard indicator for reduced-risk individuals. These results suggest that the leuco-dye of the present invention reacts with the actual metabolic activation intermediates responsible for ultimate toxic effects such as carcinogenesis.

EXAMPLE 9

Figure 6A:
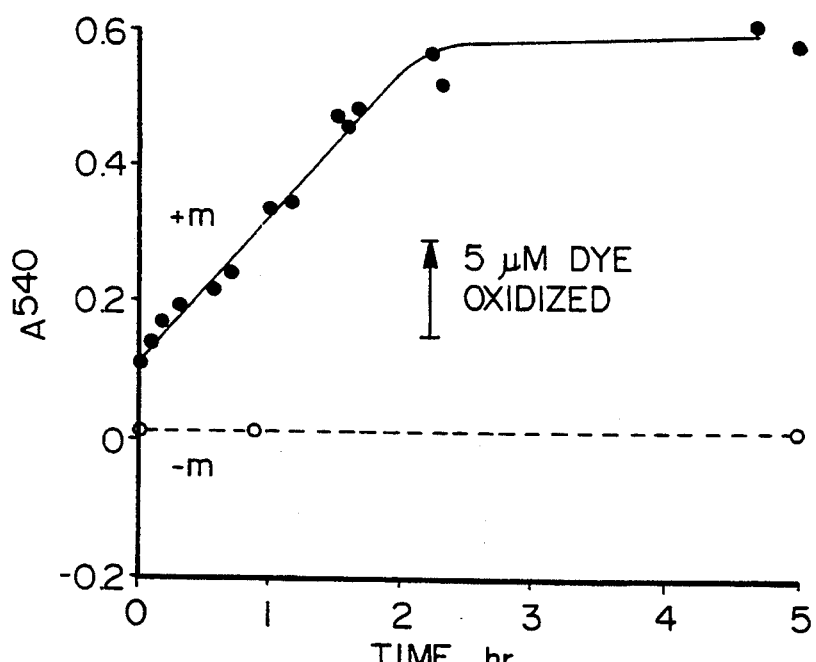
FIGS. 6a and 6b are plots of data obtained in Example 9 showing time-dependency of leuco-PRA oxidation and NADPH reduction caused by an in vitro microsomal activation of hydrazine.
Figure 6B:
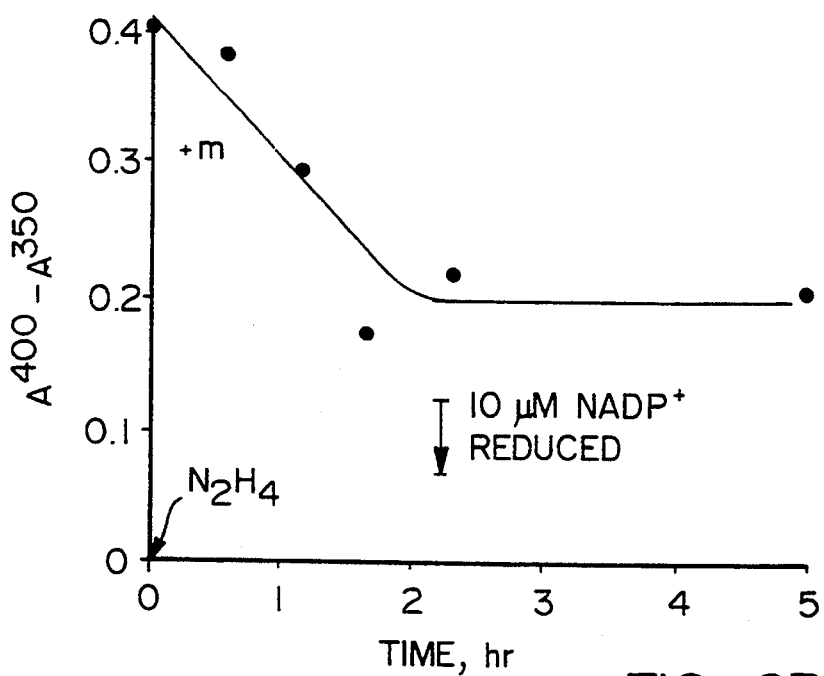

Color Development Follows Metabolic Activation of Hydrazine, but Not NADPH Concentration Change FIG. 6 shows time courses for leuco dye oxidation and simultaneous NADPH reduction, driven by the microsomal activation of drazine. Test of leuco pararosaniline color formation and NADPH redox states, as a function of time after hydrazine addition, was conducted in vitro, and UV-visible absorbance changes monitored. All systems were aerobic (at least 0.2 mM $O_2$). 0.03 mM Pararosaniline was reduced by addition of 0.1 mM sodium sulfite in 0.1 M 10 tris(hydroxymethyl)aminomethane buffer (pH=7.5), and 0.3 mM NADPH with approximately 0.5 mg/mL microsomal protein (curves indicated with "+m"). At time=0, hydrazine hydrate (pH=7.5) was added to a final concentration of 0.5 mM. Both leuco-dye oxidation and NADPH reduction proceeded linearly with time, suggesting a microsomal enzyme catalyzed mechanism for both reactions, reaching asymptotes at approximately 2.0-2.5 hours. Approximately 60% of the leuco dye was oxidized (0.02 mM) during the reaction, and roughly twice that amount of $NADP^+$ reduced to NADPH. Thus, changes in the redox state of NADPH do not correspond directly to the metabolic activation intermediate or reaction step with which the leuco dye of the present invention participates.

EXAMPLE 10

Best Mode of Detection Elements for Liquid and Vapor Phase Exposures

Detection elements of the present invention were prepared in the following manner. 13 mg PRA dissolved in 9.8 mL 0.1M TRISMOPS buffer (pH=7.4) and 3.2 mL ethanol, was bleached with 71 mg solid sodium sulfite. 0.05 mL Aliquots of the leuco-dye solution were plied to sheets of transparency film, and were air dried for one hour. Subsequently, a suspension containing in a total volume of 15 mL, 2 mM NADPH and 1.33 mg/mL of 300 Bloom porcine skin gelatin, plus 5 mL of benzo(a)pyrene-induced rat liver microsomes (obtained from a rat which had been injected peritoneally with a benzo(a)pyrene solution approximately 24 hours prior to sacrifice), was plied in 0.05 mL aliquots over the dried leuco-dye test spots. After drying in air, the test spots were cut and mounted in 35 mm tissue culture dishes, then stored at −20° C. until ready for use. Detection elements were visually clear, with a slight flesh tone.

Figure 7:
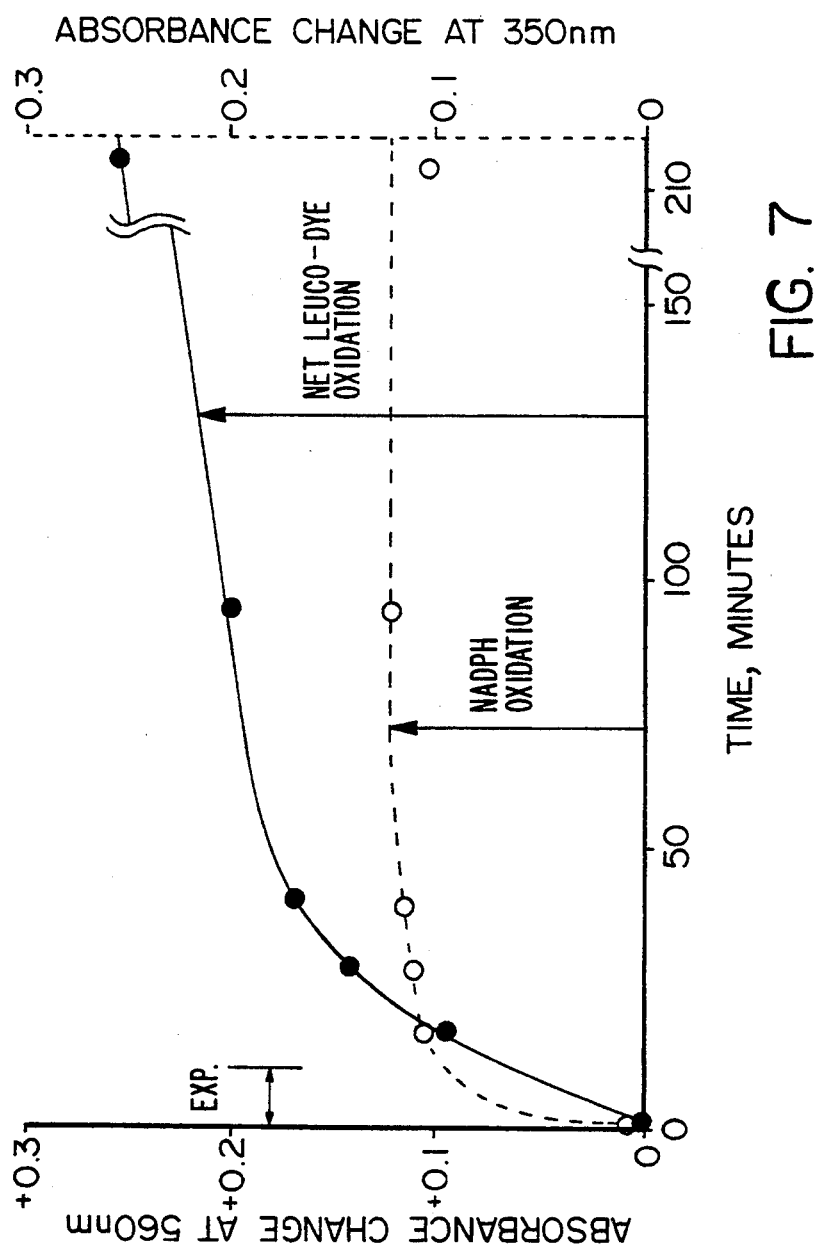
FIG. 7 is a plot of data obtained in Example 10 showing time-dependent absorbance changes (leuco dye oxidation) in detection elements of the present invention exposed to vapors of the carcinogen chloromethyl methyl ether, together with a plot of corresponding NADPH oxidation data.

Vapor exposures of detection elements to the carcinogen chloromethyl methyl ether ($CH_3$—O—$CH_2Cl$) were carried out at ambient temperature, pressure, and humidity conditions in a continuous flow chamber. Air, metered at a flow rate of 1 L/min, was passed through a flask containing 2.0 mL of a rapidly stirred solution of $CH_3$—O—$CH_2Cl$ in ethanol. After a glass wool plug to remove entrained liquid mists, the loaded air stream entered a 10 mm diameter tube into which the detection elements were mounted, without pre-moistening, parallel to the air flow. Flow conditions were calculated to be laminar (estimated Reynolds number=150) under these conditions. Exposure was conducted for ten minutes, after which the detection elements were removed and analyzed colorimetrically by taping to the sample beam exit slit of a double-beam spectrophotometer, and scanning the absorption spectrum versus an unexposed detection element affixed to the reference beam. At one exemplary test condition, in which the initial solution concentration of $CH_3$—O—$CH_2Cl$ was 1.2M, 0.4 mL of the starting solution was recovered at the end of the exposure period. Based on both material balance and Raoult's law calculations, a single value of approximately 5200 ppm was determined for the airborne concentration of $CH_3$—O—$CH_2Cl$ during the exposure. FIG. 7 shows the absorbance changes for the detection element during the 10-minute exposure period, and for a 2.5 hour period following. NADPH oxidation, equivalent to 0.4 mM or approximately 20% of the total NADPH, occurred during the 10-minute exposure, but ceased thereafter. By contrast, leuco-dye oxidation continued to intensify for some 2-4 hours, to a final level of about 0.5 mM in the detection element. Control runs, in which ethanol solvent was vaporized but $CH_3$—O—$CH_2Cl$ was absent from the system, did not indicate significant oxidation of NADPH in the detection element. FIG. 7 kinetics show that leuco-PRA reacts with a secondary or tertiary metabolic intermediate downstream from the initial NADPH-driven activation reaction.

The present example, in which the net redox change of NADPH proceeds in the same direction as the leuco-dye oxidation associated with $CH_3$—O—$CH_2Cl$ exposure, contrasts starkly with the Example 9 result, in which the net redox change of NADPH proceeded in the opposite direction from the leuco-dye oxidation associated with hydrazine exposure. The visible/colorimetric response of the present invention to both toxic carcinogens proceeds in a common consistent manner, despite the fact that NADPH chemistry proceeds in opposite directions.

Figure 8:
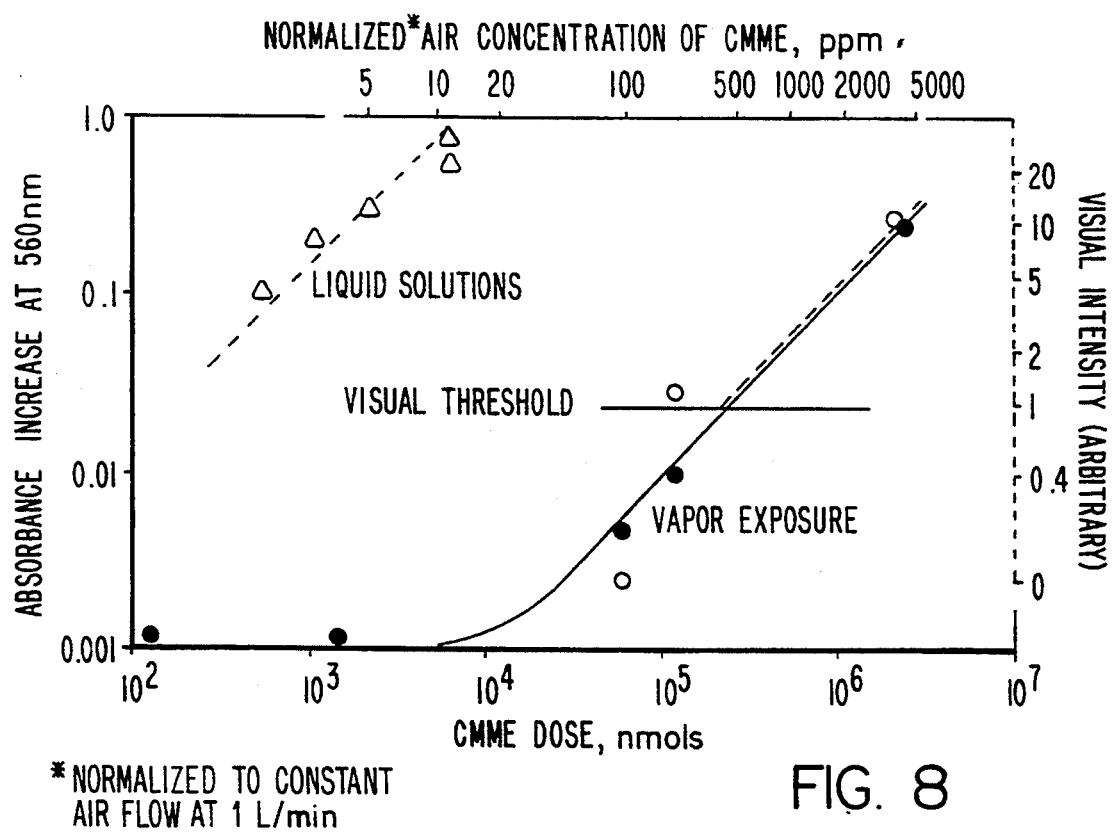
FIG. 8 is a plot of data obtained in Example 10 in an experiment similar to that corresponding to FIG. 7, wherein the airborne concentration of chloromethyl methyl ether was adjusted by lowering its solution concentration, and color development of detection elements according to the present invention was observed to be proportional to dose of the chemical, whether by direct liquid exposure or by exposure to vapor.

In similar experiments to FIG. 7, but in which the airborne concentration of $CH_3$—O—$CH_2Cl$ was adjusted by lowering its solution concentration, color development is proportional to delivered dose, both by direct liquid administration and vapor exposure. FIG. 8 shows the results. For a 10-minute exposure, approximately 0.1% of the total $CH_3$—O—$CH_2Cl$ in the air stream is absorbed and reacted by detection elements mounted parallel to the air flow. Longer exposure periods, and/or a more direct-facing orientation, are expected to significantly increase the absorption efficiency.

EXAMPLE 11

Figure 9:
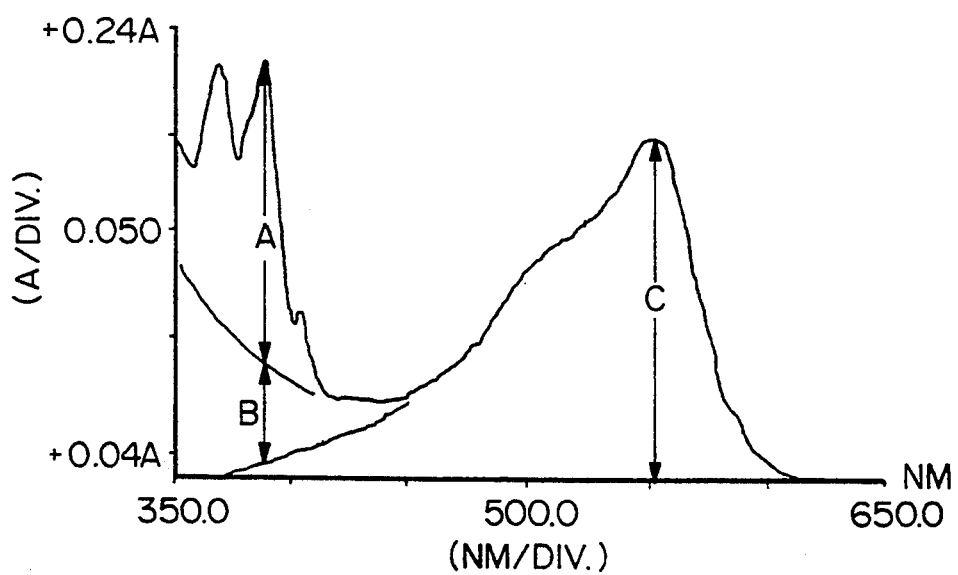
FIG. 9 is a plot of absorbance versus exposure concentration data obtained in Example 11 in which detection elements according to the present invention were used to conduct wiping tests of clothing exposed to known concentrations of benzo(a)pyrene and phenol.

Best Mode of Detection Elements for Determination of Waterborne or Surface Chemical Hazards Detection elements prepared essentially by the method of Example 10 above, without the mounts, were used to conduct wipe tests of personal protective clothing exposed to carcinogenic chemical mixtures. A glove coated with a solution of 0.002 mmols benzo(a)pyrene and 0.38 mmols phenol over a 1000 $mm^2$ area was donned, doffed and weighed nine times, then donned a tenth time, at which time a 12 mm diameter detection element was streaked over a 12 mm length of the glove. The gravimetrically determined incident dose to the detection element was equal to or less than 0.00046 mmols benzo(a)pyrene and 0.088 mmols phenol. From the visual intensity and optical density measurements as in Example 6, coupled with the dose-response standard curves for benzo(a)pyrene and phenol as in Table 6 of Example 7, an absorbed dose of lee nmols benzo(a)pyrene and 300–1000 nmols phenol is estimated. FIG. 9 shows an absorption spectrum of the exposed detection element, obtained by the same method as in Example 10. Triplet peaks between 350–400 nm (A, FIG. 9) are due to residual benzo(a)pyrene absorbed by the detection element. An absorption band in the same region due to 1,4-benzoquinone (B, FIG. 9) is also present. The broad absorption peak centered near 550 nm (C, FIG. 9) is due to the pigment reaction of the C-Probe dye. Residual unmetabolized benzo(a)pyrene was 7 nmols; phenol metabolites, as 1,4-benzoquinone were on the order of 20 nmols. Dye color was on the order of <10 nmols. Thus the estimated metabolized dose was approximately 93 nmols benzo(a)pyrene and 20 nmols phenol. Since a significant portion (about ⅓) of the microsomes employed in the preparation of the detection elements were obtained from rat liver induced with benzo(a)pyrene, as in Example 10 above, the accelerated metabolism of benzo(a)pyrene is expected.

EXAMPLE 12

Wipe Test of Contaminated Protective Clothing

Detection elements prepared as in Examples 10 and 11 were streaked over 10–25 mm lengths of firefighters' suits comprised of fabric marketed under the trade name "NOMEX", or were dipped into spent wash water samples from a commercial cleaning operation, and the resulting color development was read visually as in Example 6. Thus, a detection element streaked, without pre-moistening, over a suit contaminated with absorbed smoke developed color with a visual intensity of "3," whereas unexposed detection elements possessed color intensity of "0–1." Two pre-moistened detection elements streaked over a contaminated suit developed color with respective visual intensities of "3" and "7." A detection element streaked, without pre-moistening, over a fire suit which had been cleaned to remove smoke contamination retained a "0" visual intensity, and did not develop coloration. Similarly, a premoistened detection element streaked over a cleaned fire suit gave coloration equivalent to a "1" visual intensity, which was indistinguishable from the unexposed controls. Two detection elements dipped into samples of spent wash water and immediately removed, developed coloration corresponding to respective visual intensities of "4–5" and "5–6."

EXAMPLE 13

Opportunistic Detection of Fugitive Pesticide Emissions

During a partial building treatment for termite infestation, thirteen detection elements of the present invention were deployed for room-by-room area monitoring in a split-level office building (approximately 600 sq ft on each level). Detection elements were read visually after 2.5-hours and 20-hours following introduction of a commercial formulation marketed under the trade name "PRYFON" into the foundation along one side of the structure. Specifically, a detection element placed 0.3 m below a drilling point, at the outside wall at 4° C., developed strong coloration (e.g., visual intensity of "7–10") within 2.5 hours. A second detection element placed on a desk top in an upper level office, 1.7 m directly above the drilling point, developed coloration (e.g., visual intensity of "5–7") within 2.5 hours. Two detection elements, placed on a window sill on the same wall but in an adjacent room approximately 4–5 m from the previously mentioned detection element, developed signicant coloration (visual intensity of "3–4" after 2.5 hours, and "7" after 20 hours exposure). A detection element placed on a table in the lower level office, at 0.6 m directly below the drilling point, did not develop significant coloration (e.g., visual intensity <"1–2") within 20 hours. A second detection element placed in the lower level office, at a distance of 6–7 m from the one previously described, likewise did not develop significant coloration. Effusion of pesticide vapor was thus detected in the upper level rooms along the treated wall, corresponding to a maximum dose of 500 nmols "crude malathion equivalents" (or 0.2 ppm maximum airborne concentration), based on dose-response curves as in Examples 6 and 7, but was not observed anywhere in the lower level offices. Airborne concentrations decayed over a 1–2 day period following the treatment, to a level below the detection threshold of the detector elements of the present invention.

EXAMPLE 14

Preparation of a Low-Potential Analog of Cytochrome P450 Reductase

A solution of 11.12 mols $CaCl_2$ in boiled water was mixed dropwise over a 4 hour period with a deoxygenated aqueous solution containing 11.14 mols of sodium phosphate, 0.49 mols thioproline, and 0.37 mols sodium molybdate, total volume, 12 L. During this time four equal 150 mL aliquots of 0.5M $FeCl_3$ in 2-propanol and 110 mL aliquots of 0.47 M $Na_2S$ and 0.45M cysteine and 0.5M thioproline in 2-propanol were admixed with the calcium-phosphate-molybdate suspension. The resulting precipitate possessed a maroon-brown color with some greenish-black inclusions, and was collected and washed. This material was designed to mimic molydenum-containing iron-sulfur proteins such as xanthine oxidase, and to some extent, ferredoxin-type centers including NADPH-cytochrome-P450 reductase. This procedures was intended to minimize the risk of producing the functionally inactive oxo-bridge dimer Mo(V)-O-Mo(V) in the catalyst.

The resulting catalyst was analyzed for its ability to drive either the generation or the breakdown of superoxide anion radical ($O_{2-}$, ), by means of reaction with cytochrome c followed colorimetrically. Addition of 24 mg the solid catalyst to 10 mL of a 0.055 mM solution of reduced cytochrome c in the presence of air had no effect on the rate of oxidation of the cytochrome c. Thus, the catalyst appeared to possess little if any activity with respect to superoxide breakdown. In a second test, 17 mg of the solid catalyst were added to 10 mL of a 0.055 mM solution of oxidized cytochrome c containing approximately 10 mM xanthine in the presence of air. Oxygen-dependent reduction of the oxidized cytochrome c was observed, at a catalytic rate of at least 0.3 nmols per hour per mg of catalyst. Thus, the mixed-valence molybdenum iron-sulfur catalyst of the present example functions as a superoxide generator. Its rate in this capacity is approximately 1/1000 that conventionally reported for the enzyme xanthine oxidase. Because the $E_{m7}$ for superoxide anion radical is on the order of −0.32 V, the active centers in this synthetic molybdenum iron-sulfur catalyst can be concluded to possess low redox potentials, in keeping with the known properties of ferredoxin-type enzymes and NADPH-cytochrome P450 reductase.

We claim:

1. A method of determining metabolic activation of a potentially toxic or carcinogenic substance as an indication of its potential toxic or carcinogenic activity, which comprises the steps of:
   (a) contacting molecules of said substance with an in vitro mixture contained in dispersed condition in a film layer of a hydrophilic film-forming agent at pH between 5 and 9 in the presence of moisture absorbed by said hydrophilic film, said mixture comprising cytochrome P450 complexes comprising cytochrome P450 oxidases, molecules of NADPH, and reductase complexes selected from a group consisting of cytochrome P450 reductase complexes and ferredoxin complexes, to thereby effect metabolic activation of said substance having toxic or carcinogenic activity; and
   (b) colorimetrically detecting said metabolic activation of said substance by means of a change in color of a chemically reduced precursor form of a low redox potential dye relatively stable against spontaneous oxidation in air, which is convertible to a different color by oxidative events associated with said metabolic activation.

2. The method of claim 1 wherein said cytochrome P450 complexes consist essentially of microsome preparations.

3. The method of claim 2 wherein said cytochrome P450 complexes are enriched by induction with cytochrome P450IA1.

4. The method of claim 1 wherein said cytochrome P450 complexes comprise molecules of a synthetic analog of cytochrome P450 reductase comprised of a trinuclear iron-sulfur complex alone or embedded in a calcium-phosphate matrix.

5. The method of claim 1 wherein said dye precursor is of a di- or tri-phenylmethane dye.

6. A self-contained detecting element for detecting molecules of a chemical substance with potential toxic or carcinogenic activity comprising:
   a first film layer of a hydrophilic film-forming agent at a pH between 6 and 9;
   an in vitro biological-material having a cytochrome P450 activity dispersed within said first film layer, said biological material comprising cytochrome P450 complexes, reductase complexes selected from a group consisting of cytochrome P450 reductase complexes and ferredoxin complexes, and molecules of NADPH; and
   molecules of a chemically reduced precursor form of a low redox potential dye that is relatively stable against spontaneous oxidation in air, the precursor form being convertible to a different color by oxidative events associated with action of the cytochrome P450 complexes on molecules of a chemical substance to be tested, said precursor form being contained in dispersed condition either in the first film layer or in a second film layer of said film-forming agent in contact with said first film layer directly or through at least one additional film layer of said film-forming agent in direct contact with the first and second film layers whereby, upon exposure of said element to said chemical substance, said element exhibits a color change to said different color.

7. The element of claim 6 wherein said biological material is obtained from cells selected from a group consisting of liver cells, lung cells, and fibroblast cells.

8. The element of claim 7 wherein said biological material is enriched by induction with cytochrome P450IA1.

9. The element of claim 6 wherein said biological material comprises microsomes.

10. The element of claim 6 wherein said precursor form is of a di- or tri-phenylmethane dye.

11. The element of claim 10 wherein said precursor is maintained in a chemically reduced state in the presence of air by the presence of a 1–100 fold molar excess of NADPH and a salt of sulfite and an alkali metal.

12. The element of claim 6 wherein said biological material and said precursor form of said dye are contained in a common film layer.

13. The element of claim 6 wherein said biological material and said precursor form of said dye are contained in separate film layers of said film-forming agent, which layers being in contact with each other.

14. A method as recited in claim 1 wherein the precursor is dispersed in the same film layer as the mixture.

15. A method as recited in claim 1 wherein the precursor is dispersed in a separate film layer of the film-forming agent in contact with the film layer containing the mixture.

16. A method as recited in claim 2 wherein the microsome preparations are obtained from eucaryotic cells selected from a group consisting of liver cells, lung cells, and fibroblasts.

17. A method of determining metabolic activation of a potentially toxic or carcinogenic substance as an indication of its potential or carcinogenic activity, which comprises the steps of:
   (a) contacting molecules of the substance with an in vitro mixture contained in a first film layer of a hydrophilic film-forming agent at pH between 5 and 9 in the presence of moisture absorbed by the hydrophilic film, the mixture comprising cytochrome P450 complexes, NADPH molecules, and NADPH-cytochrome P450 reductase enzymes, to thereby effect metabolic activation of molecules of the substance contacting the first film layer; and
   (b) colorimetrically detecting the metabolic activation of molecules of the substance by the mixture by means of a change in color of a chemically reduced precursor form of a low redox potential dye that is relatively stable against spontaneous oxidation in air, the precursor being convertible to a different color by oxidative events associated with said metabolic activation.

* * * * *

UNITED STATES PATENT AND TRADEMARK OFFICE
CERTIFICATE OF CORRECTION

PATENT NO. : 5,413,915

DATED : May 9, 1995

INVENTOR(S) : CASE ET AL.

It is certified that error appears in the above-identified patent and that said Letters Patent is hereby corrected as shown below:

On the Cover Page:

Under the heading "[56] References Cited - OTHER PUBLICATIONS," page 2, second column, line 22, "*Bicillus*" should be --*Bacillus*--.

Column 8, line 43, "80° C" should be -- -80° C--.

Column 20, line 28, "bioavail-ability" should be --bioavailability--.

Column 21, line 47, "measurement" should be --measurements;--.

Column 22, line 5, "aidehyde" should be --aldehyde--.

Column 22, line 13, "reducive" should be --reductive--.

Column 22, line 14, "oxidarive" should be --oxidative--.

Column 26, line 27, in footnote 7 of Table 5, "p-bis[2-(4-phenoxyazolyl)]-benzene" should be -- p-bis[2-(5-phenoxyazolyl)]-benzene--.

Column 26, line 43, "10" should be deleted.

Column 27, line 23, "86-103 ," should be -- 86-103,--.

UNITED STATES PATENT AND TRADEMARK OFFICE
CERTIFICATE OF CORRECTION

PATENT NO. : 5,413,915
DATED : May 9, 1995
INVENTOR(S) : CASE ET AL.

It is certified that error appears in the above-identified patent and that said Letters Patent is hereby corrected as shown below:

Column 28, line 42, after the chart labeled "Carcinogenicity" and before Table 6, insert:

--Data in parentheses: Study sample with crude pesticides omitted. Prevalence-corrected accuracy (Tk) = 66% (67%). Agreement with gross accuracy indicates that study sample is comparable to any other sample.--

Column 29, item 37 of Table 6, "+$^a$" should be -- +$^a$ --.

Column 29, item 40 of Table 6, the second occurrence of "-$^a$" should be -- -$^a$ --.

Column 29, item 41 of Table 6, "-$^a$" should be -- -$^a$ --.

Column 35, line 68, "Solid symbols" should be underlined: --<u>Solid symbols</u>--.

Column 36, line 5, "Open symbols" should be underlined: --<u>Open symbols</u>--.

Column 36, line 7, "Triangles" should be underlined: --<u>Triangles</u>--.

Column 36, line 8, "Circles" should be underlined: --<u>Circles</u>--.

UNITED STATES PATENT AND TRADEMARK OFFICE
CERTIFICATE OF CORRECTION

PATENT NO. : 5,413,915
DATED : May 9, 1995
INVENTOR(S) : CASE, et al

It is certified that error appears in the above-indentified patent and that said Letters Patent is hereby corrected as shown below:

Column 37, line 14, "drazine" should be --hydrazine--.

Column 39, line 6, "lee" should be --100--.

Signed and Sealed this

Sixteenth Day of April, 1996

Attest:

BRUCE LEHMAN

Attesting Officer

Commissioner of Patents and Trademarks